(12) United States Patent
Lee

(10) Patent No.: US 9,012,191 B2
(45) Date of Patent: Apr. 21, 2015

(54) DRY GRIND ETHANOL PRODUCTION PROCESS AND SYSTEM WITH FRONT END MILLING METHOD

(75) Inventor: Chie Ying Lee, Fremont, CA (US)

(73) Assignee: Lee Tech LLC, Fremont, CA (US)

( * ) Notice: Subject to any disclaimer, the term of this patent is extended or adjusted under 35 U.S.C. 154(b) by 0 days.

(21) Appl. No.: 13/428,263

(22) Filed: Mar. 23, 2012

(65) Prior Publication Data

US 2012/0244590 A1 Sep. 27, 2012

Related U.S. Application Data

(60) Provisional application No. 61/466,985, filed on Mar. 24, 2011, provisional application No. 61/501,041, filed on Jun. 24, 2011.

(51) Int. Cl.
| | |
|---|---|
| *C12P 7/06* | (2006.01) |
| *C12M 1/00* | (2006.01) |
| *C12M 1/33* | (2006.01) |
| *C12P 19/02* | (2006.01) |
| *C12P 19/14* | (2006.01) |
| *C12P 7/10* | (2006.01) |

(52) U.S. Cl.
CPC ............... *C12M 21/12* (2013.01); *C12M 45/02* (2013.01); *Y02E 50/17* (2013.01); *C12P 19/02* (2013.01); *C12P 19/14* (2013.01); *C12P 7/10* (2013.01); *C12P 2203/00* (2013.01)

(58) Field of Classification Search
None
See application file for complete search history.

(56) References Cited

U.S. PATENT DOCUMENTS

| 2,132,250 A | * | 10/1938 | Wagner | ........................ 435/162 |
| 2,698,826 A | | 1/1955 | Peltzer, Sr. | |

(Continued)

FOREIGN PATENT DOCUMENTS

| CN | 101795578 A | 8/2010 |
| WO | 2004008838 A2 | 1/2004 |

(Continued)

OTHER PUBLICATIONS

Wahjudi et al., Cereal Chem. 77(5): 640-644 (2000).*

(Continued)

*Primary Examiner* — Patricia A Leith
*Assistant Examiner* — Erin M Bowers
(74) *Attorney, Agent, or Firm* — Wood, Herron & Evans, LLP

(57) ABSTRACT

A dry grind ethanol production process and system with front end milling method is provided for improving alcohol and/or by-product yields, such as oil and/or protein yields. In one example, the process includes grinding corn kernels into particles then mixing the corn particles with a liquid to produce a slurry including oil, protein, starch, fiber, germ, and grit. Thereafter, the slurry is subjected to a front end milling method, which includes separating the slurry into a solids portion, including fiber, grit, and germ, and a liquid portion, including oil, protein, and starch, then milling the separated solids portion to reduce the size of the germ and grit and release bound starch, oil, and protein from the solids portion. The starch is converted to sugar, and alcohol is produced therefrom then recovered. Also, the fiber can be separated and recovered. Oil and protein may be separated and recovered as well.

18 Claims, 17 Drawing Sheets

(56) References Cited

U.S. PATENT DOCUMENTS

| | | | |
|---|---|---|---|
| 3,251,717 | A | 5/1966 | Honeychurch et al. |
| 3,909,288 | A | 9/1975 | Powell et al. |
| 4,181,748 | A | 1/1980 | Chwalek et al. |
| 4,207,118 | A | 6/1980 | Bonnyay et al. |
| 4,255,518 | A * | 3/1981 | Muller et al. .......... 435/161 |
| 4,361,651 | A | 11/1982 | Keim |
| 4,495,207 | A * | 1/1985 | Christianson et al. ........ 426/312 |
| 4,501,814 | A | 2/1985 | Schoenrock et al. |
| 7,494,675 | B2 | 2/2009 | Abbas et al. |
| 7,682,812 | B2 | 3/2010 | Verser et al. |
| 2005/0255190 | A1 * | 11/2005 | Mehra et al. .......... 426/11 |
| 2008/0220125 | A1 | 9/2008 | Abbas et al. |
| 2008/0279983 | A1 * | 11/2008 | Lohrmann et al. .......... 426/44 |
| 2009/0005539 | A1 | 1/2009 | Scheimann et al. |
| 2009/0029432 | A1 | 1/2009 | Abbas et al. |
| 2009/0047715 | A1 | 2/2009 | Cates et al. |
| 2010/0012596 | A1 | 1/2010 | Lee |
| 2010/0016554 | A1 | 1/2010 | Cheryan |
| 2010/0055741 | A1 | 3/2010 | Galvez, III et al. |
| 2010/0059609 | A1 | 3/2010 | Teeter, Jr. et al. |
| 2010/0260918 | A1 | 10/2010 | Wang et al. |

FOREIGN PATENT DOCUMENTS

| | | | |
|---|---|---|---|
| WO | 2006055489 | A2 | 5/2006 |
| WO | 2009015333 | A1 | 1/2009 |
| WO | 2010138110 | A1 | 12/2010 |

OTHER PUBLICATIONS

Xu et al., Carbohydrate Polymers 76: 521-527 (2009).*

International Search Report issued in International Patent Application No. PCT/US12/30337, dated Sep. 7, 2012, 13 pages.

Chinese Patent Office, Office Action issued in corresponding Chinese Patent Application No. 201280023265.2 and English-language translation (Sep. 24, 2014) (19 pages).

Guo, Jian, "The Process and Equipment of Slurry-residue Separation in Cassava Starch Production," Journal of Longyan Teachers College, vol. 22, No. 3 (Jun. 30, 2004) (2 pages).

Internationa Bureau of WIPO, International Preliminary Report on Patentability and Written Opinion issued in corresponding International Patent Application No. PCT/US2012/030337 (Sep. 24, 2013) (8 pages).

European Patent Office, Supplementary European Search Report issued in corresponding European Patent Application No. 12 76 0279 (Nov. 14, 2014) (8 pages).

Dien Bruce S., et al. "Fermentation of "Quick Fiber" Produced from a Modified Corn-Milling Process into Ethanol and Recovery of Corn Fiber," Applied Biochemistry and Biotechnolgy Spring 2004, ISSN: 0273-2289, vol. 113-116, pp. 937-949 (Apr. 2004) (14 pages).

* cited by examiner

DRY GRIND ETHANOL PRODUCTION PROCESS AND SYSTEM WITH FRONT END MILLING METHOD

CROSS REFERENCE TO RELATED APPLICATIONS

This application claims the benefit of U.S. Provisional Application No. 61/466,985, filed Mar. 24, 2011, and U.S. Provisional Application No. 61/501,041, filed Jun. 24, 2011, the disclosures of which are hereby incorporated by reference herein in its entirety.

TECHNICAL FIELD

The present invention relates generally to dry mill alcohol production and, more specifically, to improved milling methods and systems for dry grind ethanol plants to increase alcohol and/or by-product yields.

BACKGROUND

One alcohol of great interest today is ethanol. Most of the fuel ethanol in the United States is produced from a wet mill process or a dry grind ethanol process. Although virtually any type and quality of grain can be used to produce ethanol, the feedstock for these processes is typically corn.

The conventional processes for producing various types of alcohol from grain generally follow similar procedures. Wet mill corn processing plants convert corn grain into several different co-products, such as germ (for oil extraction), gluten feed (high fiber animal feed), gluten meal (high protein animal feed), and starch-based products such as ethanol, high fructose corn syrup, or food and industrial starch. Dry grind ethanol plants generally convert corn into two products, namely ethanol and distiller's grains with solubles. If sold as wet animal feed, distiller's wet grains with solubles are referred to as DWGS. If dried for animal feed, distiller's dried grains with solubles are referred to as DDGS. In the standard dry grind ethanol process, one bushel of corn yields approximately 8.2 kg (approximately 17 lbs.) of DDGS in addition to the approximately 10.5 liters (approximately 2.8 gal) of ethanol. This co-product provides a critical secondary revenue stream that offsets a portion of the overall ethanol production cost.

With respect to the dry grind process, FIG. 1 is a flow diagram of a typical dry grind ethanol production process 10. As a general reference point, the dry grind ethanol process 10 can be divided into a front end and a back end. The part of the process 10 that occurs prior to distillation and dehydration 24 is considered the "front end", and the part of the process 10 that occurs after distillation and dehydration 24 (hereinafter "dehydration") is considered the "back end". To that end, the front end of the process 10 begins with a grinding step 12 in which dried whole corn kernels are passed through hammer mills for grinding into meal or a fine powder. The screen openings in the hammer mills typically are of a size 7/64, or about 2.78 mm, with the resulting particle distribution yielding a very wide spread, bell type curve, which includes particle sizes as small as 45 micron and as large as 2 to 3 mm.

The grinding step 12 is followed by a liquefaction step 16 whereat the ground meal is mixed with cook water to create a slurry and a commercial enzyme called alpha-amylase is typically added (not shown). The pH is adjusted here to about 5.8 to 6 and the temperature maintained between about 50° C. to 105° C. so as to convert the insoluble starch in the slurry to soluble starch. Various typical liquefaction processes, which occur at this liquefaction step 16, are discussed in more detail further below. The stream after the liquefaction step 16 has about 30% dry solids (DS) content with all the components contained in the corn kernels, including sugars, protein, fiber, starch, germ, grit, and oil and salts, for example. There generally are three types of solids in the liquefaction stream: fiber, germ, and grit, with all three solids having about the same particle size distribution.

The liquefaction step 16 is followed by a simultaneous saccharification and fermentation step 18. This simultaneous step is referred to in the industry as "Simultaneous Saccharification and Fermentation" (SSF). In some commercial dry grind ethanol processes, saccharification and fermentation occur separately (not shown). Both individual saccharification and SSF can take as long as about 50 to 60 hours. Fermentation converts the sugar to alcohol using a fermentor. Subsequent to the saccharification and fermentation step 18 is the distillation (and dehydration) step 24, which utilizes a still to recover the alcohol.

Finally, the back end of the process 10, which follows distillation 24, includes a centrifugation step 26, which involves centrifuging the residuals, i.e., "whole stillage", produced with the distillation step 24 to separate the insoluble solids ("wet cake") from the liquid ("thin stillage"). The "wet cake" includes fiber, of which there are three types: (1) pericarp, with average particle sizes typically about 1 mm to 3 mm; (2) tricap, with average particle sizes about 500 micron; (3) and fine fiber, with average particle sizes of about 250 micron. The liquid from the centrifuge contains about 6% to 8% DS.

The thin stillage enters evaporators in an evaporation step 28 to boil away moisture, leaving a thick syrup that contains the soluble (dissolved) solids from fermentation (25% to 40% dry solids). The concentrated slurry may be subjected to an optional oil recovery step 29 whereat the slurry can be centrifuged to separate oil from the syrup. The oil can be sold as a separate high value product. The oil yield is normally about 0.4 lb./bu of corn with high free fatty acids content. This oil yield recovers only about ¼ of the oil in the corn. About one-half of the oil inside the corn kernel remains inside the germ after the distillation step 24, which cannot be separated in the typical dry grind process using centrifuges. The free fatty acids content, which is created when the oil is held in the fermenter for approximately 50 hours, reduces the value of the oil. The (de-oil) centrifuge only removes less than 50% because the protein and oil make an emulsion, which cannot be satisfactorily separated.

The centrifuged wet cake and the syrup, which has more than 10% oil, can be mixed and the mixture may be sold to beef and dairy feedlots as Distillers Wet Grain with Soluble (DWGS). Alternatively, the syrup can be mixed with the wet cake, then the concentrated syrup mixture may be dried in a drying step 30 and sold as Distillers Dried Grain with Soluble (DDGS) to dairy and beef feedlots. This DDGS has all the protein and 75% of the oil in corn. But the value of DDGS is low due to the high percentage of fiber, and in some cases the oil is a hindrance to animal digestion.

Further with respect to the liquefaction step 16, FIG. 2 is a flow diagram of various typical liquefaction processes that define the liquefaction step 16 in the dry grind ethanol production process 10. Again, the front end of the process 10 begins with a grinding step 12 in which dried whole corn kernels are passed through hammer mills for grinding into meal or a fine powder. The grinding step 12 is followed by the liquefaction step 16, which itself includes multiple steps as is discussed next.

Each of the various liquefaction processes generally begins with the ground meal being mixed with cook, or back set, water, which can be sent from evaporation step 28 (FIG. 1), to create a slurry at slurry tank 32 whereat a commercial enzyme called alpha-amylase is typically added (not shown). The pH is adjusted here, as is known in the art, to about 5.8 to 6 and the temperature maintained between about 50° C. to 105° C. so as to allow for the enzyme activity to begin converting the insoluble starch in the slurry to soluble starch.

After the slurry tank 32, there are normally three optional pre-holding tank steps, identified in FIG. 2 as systems A, B, and C, which may be selected depending generally upon the desired temperature and holding time of the slurry. With system A, the slurry from the slurry tank 32 is subjected to a jet cooking step 34 whereat the slurry is fed to a jet cooker, heated to 120° C., held in a U-tube for about 5 to 30 min., then forwarded to a flash tank. The jet cooker creates a sheering force that ruptures the starch granules to aid the enzyme in reacting with the starch inside the granule. With system B, the slurry is subjected to a secondary slurry tank step 36 whereat steam is injected directly to the secondary slurry tank and the slurry is maintained at a temperature from about 90° C. to 100° C. for about 30 min to one hour. With system C, the slurry from the slurry tank 32 is subjected to a secondary slurry tank-no steam step 38, whereat the slurry from the slurry tank 32 is sent to a secondary slurry tank, without any steam injection, and maintained at a temperature of about 80° C. to 90° C. for 1 to 2 hours. Thereafter, the slurry from each of systems A, B, and C is forwarded, in series, to first and second holding tanks 40 and 42 for a total holding time of about 2 to 4 hours at temperatures of about 80° C. to 90° C. to complete the liquefaction step 16, which then is followed by the saccharification and fermentation step 18, along with the remainder of the process 10 of FIG. 1. While two holding tanks are shown here, it should be understood that one holding tank or more than two holding tanks may be utilized.

To increase the alcohol yield, and generate additional revenue, for example, from oil and/or protein yields in the typical dry mill process, it would be beneficial to develop a process(es) to further break-up the initially ground germ particles and grit particles, which include mostly starch, to release more starch, oil, and/or protein therefrom. Such a process could provide for increased alcohol, oil, and/or protein yield, and produce much higher purity fiber (with less protein, starch and oil), which can be used as a raw feed stock for the paper industry and cellulosic to secondary alcohol processes.

Various dry grind systems have attempted to increase alcohol yields, for example, by focusing on the grinding aspect in the dry grind process 10. However, such systems are known not to have produced very good results. For example, with the grind systems in today's market, these systems tend to decrease the size on all of the particles (fiber, germ, and grit) at the same time and at the same rate. The resulting corn components can be difficult to separate, particularly if all of the particles, including the fiber, are ground too small, e.g., less than 300 microns. While alcohol yield may improve with smaller particle sizes, this can also produce a very wet decanter cake and dirty overflow, i.e., dirty thin stillage. And this dirty overflow can create fouling and result in lower syrup concentrations during the evaporation step 28. Lower syrup concentrations and wetter cakes also produce increased dryer loads raising the drying costs of DDGS. In contrast, if the resulting corn components are too large in size, e.g., greater than 1000 microns, the particles will not adequately convert to sugar during the liquefaction step 16 and alcohol yield, for example, will drop.

Such conventional systems also tend to focus on either grinding the entire stream or a partially separated stream in a very wet slurry form, without any dewatering prior to grinding. For grinding solid particles, the feed that is sent to the grind mill should be as dry as possible to yield maximum grinding results. Current systems also have failed to remove fine solid particle before feeding the particles to the cutting/grinding device. As such, the fine solid particles become smaller particles, i.e., too small, creating problems on the back end of the process by producing very wet cakes and dirty overflow, as discussed above.

It would thus be beneficial to provide an improved milling method(s) and system(s) for dry grind ethanol plants that can improve alcohol, oil, and/or protein yields, and generate additional revenue from oil and/or protein yields, for example, while avoiding and/or overcoming the aforementioned drawbacks.

SUMMARY

The present invention relates to to improved milling methods and systems for dry grind ethanol plants to increase alcohol and/or by-product yields. Such improved milling method(s) and system(s) for dry grind ethanol plants can improve alcohol, oil, and/or protein yields, and generate additional revenue from oil and/or protein yields.

In one embodiment, a dry grind ethanol production process is provided, which includes grinding corn kernels into particles then mixing the corn particles with a liquid to produce a slurry including oil, protein, starch, fiber, germ, and grit. Thereafter, the slurry is subjected to a front end milling method, which includes separating the slurry into a solids portion, including fiber, grit, and germ, and a liquid portion, including oil, protein, and starch, then milling the separated solids portion to reduce the size of the germ and grit and release bound starch, oil, and protein from the solids portion. The starch is converted to sugar, and alcohol is produced therefrom then recovered. Also, the fiber can be separated and recovered, and oil and protein may be separated and recovered as well.

In another embodiment, a dry grind ethanol production process is provided, which includes grinding corn kernels into corn particles, then mixing the corn particles with a liquid to form a slurry. Thereafter, an amount of the liquid is reduced from the slurry to form a wet cake then the wet cake is milled. Alcohol, fiber, oil and protein can be separated and recovered in this process as well.

In yet another embodiment, a system for dry grind ethanol production is provided, which includes a grinding device, which grinds corn kernels into particles and a slurry tank in which the corn particles mix with a liquid to produce a slurry including oil, protein, starch, fiber, germ, and grit. The system further includes a first dewatering device, which separates the slurry into a solids portion, including fiber, grit, and germ, and a liquid portion, including oil, protein, and starch. A size reduction device, which follows the first dewatering device, reduces the size of the germ and grit of the solids portion and releases bound starch, oil, and protein from the solids portion. And at least one holding tank, which aids in converting the starch to sugar is provided. The system further includes a fermentor to produce alcohol from the sugar and a still to recover the alcohol as well as a second dewatering device, which separates and recovers the fiber.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

Figure 1:
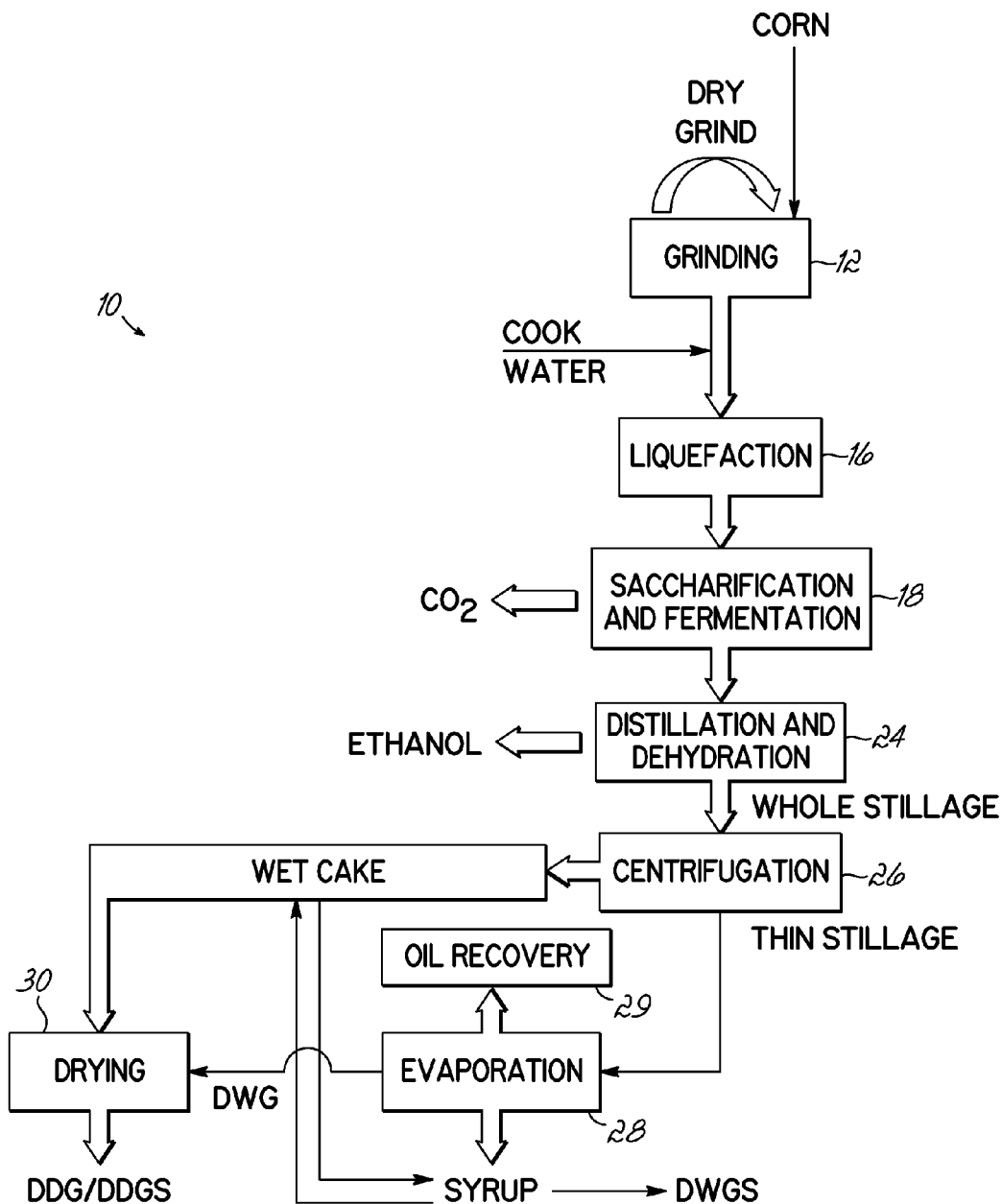
FIG. 1 is a flow diagram of a typical dry grind ethanol production process.
Figure 2:
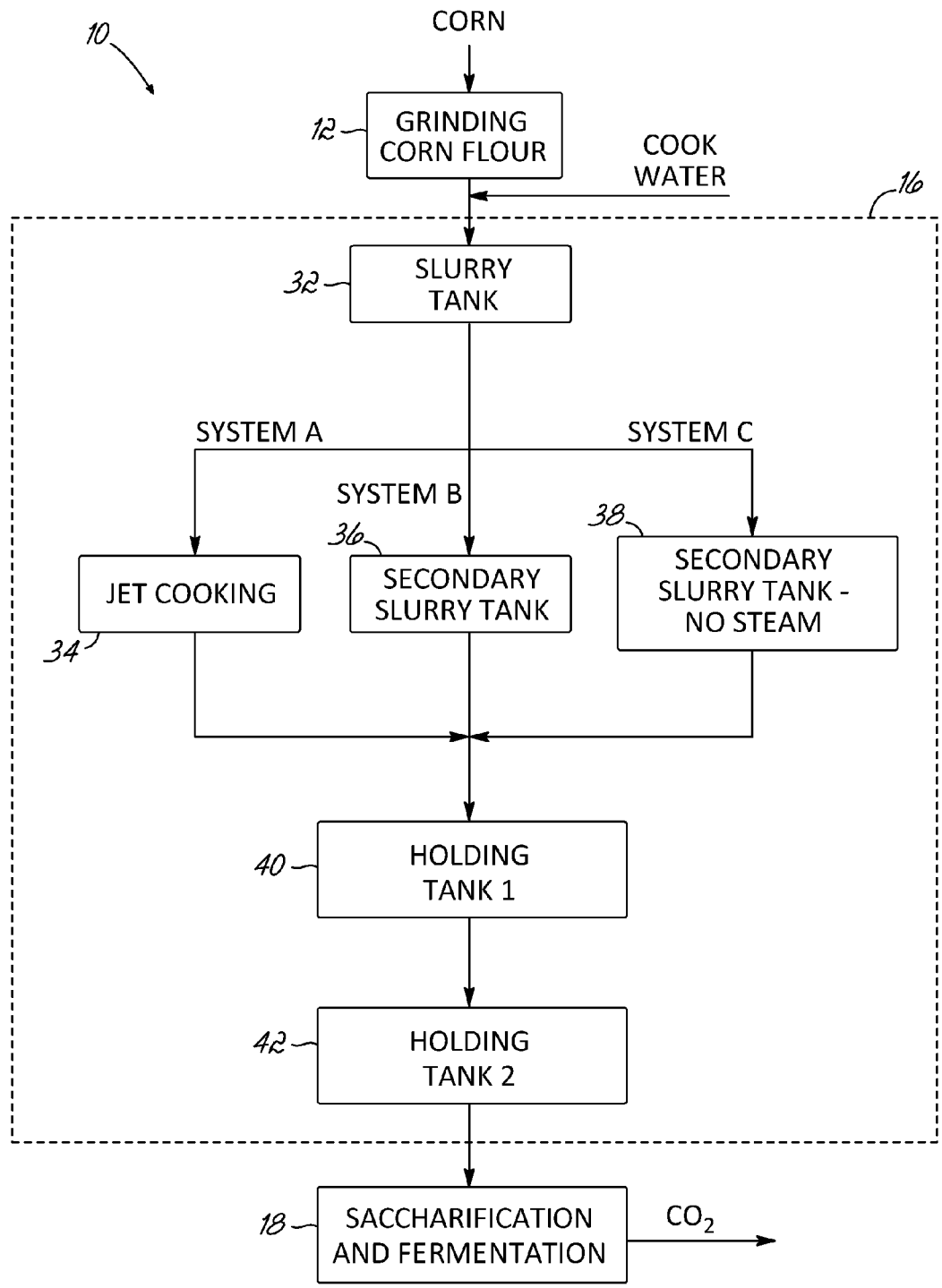
FIG. 2 is flow diagram of various typical liquefaction processes that define the liquefaction step in a dry grind ethanol production process.

FIGS. 1 and 2 have been discussed above and represent a flow diagram of a typical dry grind ethanol production process and various typical liquefaction processes that define the liquefaction step in a dry grind ethanol production process, respectively.

FIGS. 3-9B illustrate various embodiments of a dry grind ethanol production process and system with front end milling method for improving alcohol, oil and/or protein yields, and for producing a purer, more desirable fiber for secondary alcohol production, for example. These processes and systems are discussed in detail herein below.

Figure 3:
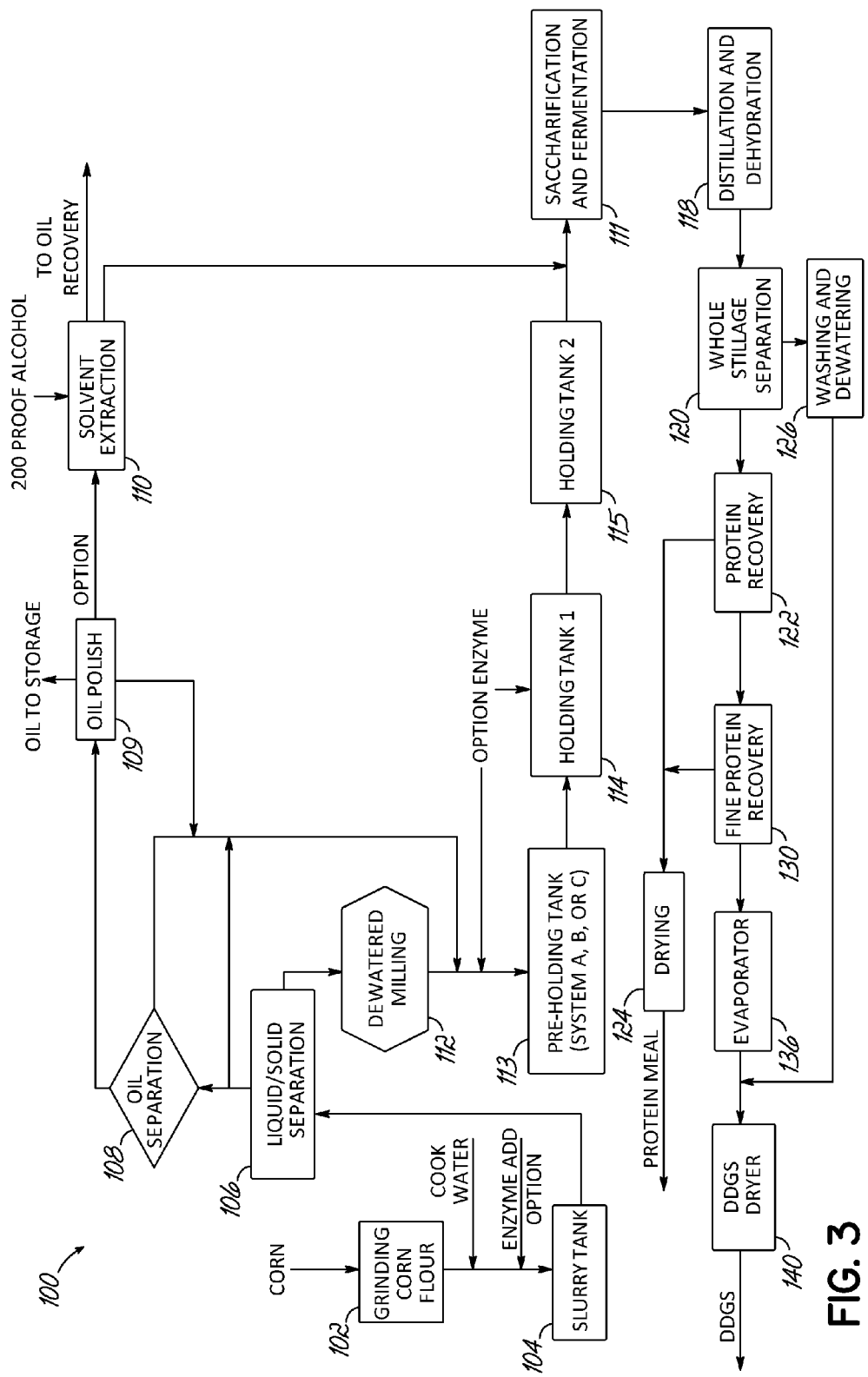
FIG. 3 is a flow diagram showing a dry grind ethanol production process and system with front end milling method in accordance with an embodiment of the invention.

With reference first to FIG. 3, this figure depicts a flow diagram of an embodiment of a dry grind ethanol production process and system with a front end milling method for improving alcohol and/or byproduct yields, e.g., oil and/or protein yields. In this process 100, corn is first subjected to a grinding step 102, which involves use of a hammer mill, or the like, to grind corn to particle sizes less than about 7/64 inch and allow for the release of oil therefrom. In one example, the screen size for separating the particles can decrease from about 7/64 inch to about 6/64 inch. In another example, the particle sizes are from about 50 micron to 3 mm. The grinding helps break up the bonds between the fiber, protein, starch, and germ.

Next, the ground corn flour is mixed with water, referred to as cook water, at slurry tank 104 to create a slurry and begin liquefaction. An enzyme(s), such as alpha amylase, optionally can be added to the slurry tank 104. The slurry may be heated at the slurry tank 104 to about 150° F. to about 200° F. for about 30 minutes to about 120 minutes. The stream from the slurry tank 104 contains about 1 lb/bu free oil and about 1.5 lb/bu germ (particle size ranges from about 50 micron to about 3 mm), 1.8 lb/bu grit (particle size ranges from about 50 micron to about 3 mm), and 4.2 lb/bu fiber (particle size ranges from about 50 micron to about 3 mm).

The feed from the slurry tank 104 is next subjected to a liquid/solid separation step 106, which defines the beginning of the front end milling method. While the front end milling method begins after the slurry tank 104 in FIG. 3, it should be understood that it may be situated at any location along the liquefaction process, including from the slurry tank 104 up to fermentation step 111. The liquid/solid separation step 106 separates a generally liquefied solution (about 60-80% by volume), which includes free oil, protein, and fine solids (which do not need grinding), from heavy solids cake (about 20-40% by volume), which includes the heavier fiber, grit, and germ, which can include bound oil, protein, and/or starch. The liquid/solid separation step 106 uses dewatering equipment, e.g., a paddle screen, a vibration screen, screen decanter centrifuge or conic screen centrifuge, a pressure screen, a preconcentrator, and the like, to accomplish separation of the solids from the liquid portion. The fine solids are no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about 1/6 to 1/2 of the screen diameter. The number of paddles on the paddle screen and the conveyor pitch on the preconcentrator can be modified depending on the amount of solids in the feed. The gap between the paddle screen and paddle can range from about 0.04 to 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 micron to 500 micron. In another example, the screen openings can range from 100 to 300 micron. In yet another example, the screen openings can range from 200 to 250 microns. Smaller screen openings tend to increase the protein/oil/alcohol yield with higher equipment and operation cost, whereas larger screen openings tend to lower protein/oil/alcohol yield with less equipment and operation cost.

The now separated liquefied starch solution can be subjected to an optional oil separation step 108, which can use any type of oil separator, such as a mud centrifuge, three phase decanter, disc decanter, three phase disc centrifuge, and the like, to separate oil from the liquefied starch solution by taking advantage of density differences. In particular, the liquefied starch solution is used as heavy media liquid to float oil/emulsion/fine germ particle. The liquefied starch solution has densities of about 1.1 to 1.2 grams/cc and 0.9 to 0.92 grams/cc for oil and 1 to 1.05 grams/cc for germ.

There can be three phases discharged from the oil separation step 108. The first is a light phase, which includes oil or an oil/emulsion layer. The second is a heavy phase, which includes the liquefied starch solution, possibly with some small germ particles. The third phase is the solid phase, which contains fine fiber, grit particle, and starch. The underflow heavy phase and solid phase can be combined as is illustrated in FIG. 3; otherwise, they can remain separated and sent to different locations for optimizing results.

The oil/emulsion/fine germ layer can be forwarded to an oil polish step 109 whereat the layer can be subjected to centrifugation, including a three phase decanter, three phase disc centrifuge, or the like to separate pure oil from the emulsion and fine germ particle. From the oil polish step 109, the emulsion and fine germ particle can be discharged as a heavy phase and optionally subjected to a solvent extraction step 110 to recover additional oil, or returned to join up with the combined starch solution/heavy phase from the oil separation step 108. At the oil polish step 109, alcohol, such as 200 proof alcohol from a distillation tower from distillation step 118, can be added to the emulsion and fine germ particles so as to break the emulsion and extract oil from the fine germ particle, which normally are less than 100 micron. The remaining fine germ particles then are sent on to fermentation step 111, as indicated.

The oil that is recovered at step 110 has a much more desirable quality in terms of color and free fatty acid content (less than 7% and, in another example, less than 5%) as compared to oil that is recovered downstream, particularly oil recovered after fermentation 111. In particular, the color of the pre-fermentation recovered oil is lighter in color and lower in free fatty acid content. The oil yield at step 108 can reach about 0.9 lb/bu whereas current oil recovery from evaporator streams average below 0.5 lb/bu. With the oil polish step 109 and solvent extraction step 110, the oil yield can increase to as high as 1.4 lb/bu.

Returning now to the liquid/solid separation step 106, the wet cake or dewatered solids portion of the stream at the liquid/solid separation step 106 (about 60 to 65% water) continues along the front end milling method and is next subjected to a dewatered milling step 112, whereat the solids, particularly the germ and grit, are reduced in size via size reduction equipment. The size reduction equipment can include a hammer mill, a pin or impact mill, a grind mill, and the like. In one example, the size reduction equipment is a pin mill or grind mill. This dewatered milling step 112 is intended to break the germ and grit particles and the bonds between fiber and starch, as well as oil and protein, without cutting the fiber too fine, thereby giving sharper separation between the fiber and protein/starch/oil.

In a dewatered form, the germ and grit particles are able to break apart more easily than the fiber as a result of increased rubbing action in which less fine fiber is created, but the germ and grit are more fully milled. This results in a relatively non-uniform particle size amongst the milled solids. For example, germ and grit particles can be milled to a particle size between about 300 to 800 microns, whereas a majority of the fiber remains within a particle size range of 500 to 2000 micron. In one example, greater than 75% of the fiber remains within a particle size range of 500 to 2000 micron. In another example, no greater than 80% by weight of the total particles after the dewatered milling step 112 have a particle size less than 800 microns. In another example, no greater than 75% by weight of the total particles after the dewatered milling step 112 have a particle size less than 800 microns. In still another example, no greater than 65% by weight of the total particles after the dewatered milling step 112 have a particle size less than 800 microns. In another example, about 30% to about 50% by weight of the total particles after the dewatered milling step 112 have a particle size from about 100 microns to about 800 microns. In still another example, about 40% to about 50% by weight of the total particles after the dewatered milling step 112 have a particle size from about 100 microns to about 800 microns. In yet another example, no greater than 50% by weight of the total particles after the dewatered milling step 112 have a particle size from about 100 microns to about 800 microns. The % protein in the solid particles that are larger than 300 micron is about 29.5%. After grind and if washing techniques are utilized, the % protein in fiber can decrease from about 29.5% to about 21.1%. The % oil in fiber can decrease from about 9.6% to about 6.4%, and the % starch in fiber can decrease from about 5.5% to about 3%.

If a grind mill is used for particle size reduction at the dewatered milling step 112, the design of the grind plates (not shown) for the grind mill can be varied to accomplish the germ and grit grinding, while tending to avoid fiber grinding. Historically, the grind plates, which are in generally opposing fashion, typically define a group of about 6 grind plate segments that form an annular ring when combined together and secured to the surface of a grind disc. Each grind plate segment and, consequently the grind plate itself, contains "tooth" designs placed in rows of annular rings or bars of various widths that extend from the inside diameter to the outside diameter of the grind plate. With bar type design grind plates, the width and depth can be varied to provide more effective grinding of the germ and grit, while tending to avoid the fiber. In one example, the bar is 20 inches long. Different combinations, numbers, and shapes and sizes of "teeth" or bar designs may be provided to more effectively grind the germ and grit, while tending to avoid the fiber. Also, the gap between the grind plates as well as the RPMs can be adjusted for desired performance and energy efficiency. In one example, the gap can be from 0.01 to 0.3 inch. In another example, the plate gap is about 0.020 to 0.15 inch. Also, in one example, the RPM can be from 900 to 3000 for one or more grind plates. In another example, the RPM is about 1800.

The grind plate may be composed of white iron, which has high abrasion resistance with approximately 25% chrome content to increase corrosion resistance, but can be formed of any suitable metal or alloy, plastic, composite, and the like.

Also the teeth size (width, height, and length), shape of the teeth, distance between teeth, and number of teeth on each row can vary to accomplish desirable germ and grit grinding, while tending to avoid fiber grinding.

One type of grind mill having a suitable type of grind plate is the FQ-136 grind mill, which is available from Fluid-Quip, Inc. of Springfield, Ohio. This type of grind mill has one 36" inch diameter stationary disc and one 36" inch diameter rotating disc. Grind plate segments defining the grind plate are installed onto each disc, and the gap between the two discs can be varied to produce an effective grind result. Grind mills can be made with larger or smaller diameter discs. The FQ-152 grind mill also available from Fluid-Quip, Inc. of Springfield, Ohio, has 52" inch diameter discs. Larger diameter discs can provide higher tangential velocity at the outside edge of the discs as compared to smaller discs, which can provide more impact and grinding or shear effect if run at the same rotational speeds. Grind mills can also be made with two rotating discs, which can vary in diameter. In this case, the discs rotate in opposite directions, producing a net effective disc to disc speed twice that of a single rotating disc. Increased speed will increase the number of teeth or bar crossings which will effect impact and/or shear effect on the medium passing through the grind mill.

If a pin/impact mill is used for particle size reduction, different pin sizes and types, e.g., round, triangular, hexagonal, and the like, can be used depending on operation requirements to optimize the dewatered milling step 112. In one example, the pin sizes can include round pins, which can be approximately 2⅛ inches in height and 1⅝ inches in diameter. Also, the RPM for the pin/impact mill can be from 2000 to 3000. The pins can be made of stainless steel or other suitable corrosion resistant metal or metal alloy, plastic, composite, and the like. One suitable type of pin/impact mill, which uses an impact force to help break the germ and grit, while tending to avoid fiber grinding, is the FQ-IM40, which is available from Fluid-Quip, Inc. of Springfield, Ohio.

After milling, which itself defines the end of the front end milling method, the solids can be mixed with the liquefied starch solution from either the optional oil separation step 108 or from the liquid/solid separation step 106, as shown, to form a heavy slurry then subjected to one of three optional pre-holding tank systems at pre-holding tank step 113, i.e., generally one of systems A, B, and C of FIG. 2. Also, if the emulsion and fine germ particle from the oil polish step 109 are not optionally subjected to the solvent extraction step 110, the underflow (mainly liquefied starch) is joined up with the underflow solution from the oil separation step 108, which is joined up with the solids from the dewatered milling step 112 to form the heavy slurry, and sent to the pre-holding tank step 113.

At pre-holding tank step 113 and as generally discussed above with respect to FIG. 2, the heavy slurry can be subjected to system A or a pressurized jet cooker and heated to about 101° C. to about 130° C. for about 3 to 30 minutes under a pressure of about 20 psi to about 150 psi, held in a U-tube for about 5 to 15 min., then forwarded to a flash tank and maintained at a temperature above 95° C. for about 3 to 30 minutes to help solubilize the starch. Alternatively, the heavy slurry can be subjected to system B or fed to a secondary slurry tank whereat steam is injected directly to the secondary slurry tank and the slurry is maintained at a temperature from about 95° C. for about 60 to 120 minutes. Alternatively, the heavy slurry can also be subjected to system C or fed to a secondary slurry tank, without steam injection, and maintained at a temperature of about 60° C. to 85° C. for 1 to 4 hours.

Thereafter, the slurry from the pre-holding tank step 113 is forwarded, in series, to first and second holding tanks 114 and 115 for a total holding time of about 2 to 4 hours at temperatures of about 60° C. to 85° C. to further solubilize the starch component in the slurry stream and complete liquefaction before sending to fermentation step 111. While two holding tanks are shown here, it should be understood that one holding tank or more than two holding tanks may be utilized.

Various enzymes (and types thereof) such as amylase or glucoamylase, fungal, cellulose, cellobiose, protease, and the like can be optionally added during and/or after the dewatered milling step 112, pre-holding tank step 113, or the holding tanks 114 and 115 to enhance the separation of components, such as to help break the bonds between protein, starch, and fiber.

After the second holding tank 115, the stream from the optional solvent extraction step 110 can be joined up with the liquefied starch slurry solution and sent to fermentation step 111 whereat fermentation occurs.

As compared with current dry milling processes, the front end milling method, which includes the liquid/solid separation step 106 and the dewatered milling step 112, gives a more complete starch conversion. In addition, an increase of about 1.0% alcohol yield, about 0.05 lb/bu oil yield, and 0.3 lb/bu protein yield can be realized.

The liquefied starch solution at fermentation step 111, which now includes the fiber, reduced grit and germ particles, as well as protein and oil, is subjected to fermentation to convert the sugar to alcohol, followed by a distillation step 118, which recovers the alcohol. At the distillation step 118, the fermented solution (normally referred to here as "beer") is separated from the whole stillage, which includes fiber, protein, oil, and germ and grit particles, to produce the alcohol. The alcohol yield is about 2.78 gal/bu, which is an increase of about 1% over conventional yields, due at least in part to the dewatered milling step 112 whereat starch in the grit and germ particle is released and eventually converted to sugar to produce more alcohol.

With continuing reference to FIG. 3, the back end of the process 100, which itself is optional insofar as a typical back end process may be utilized here, may include a whole stillage separation step 120 whereat dewatering equipment, e.g., a paddle screen, vibration screen, filtration centrifuge, pressure screen, screen bowl decanter and the like, is used to accomplish separation of the insoluble solids or "whole stillage", which includes fiber, from the liquid "thin stillage" portion. The screen openings can range in size here from about 45 to 400 micron, depending upon the purity of fiber and protein desired here. In one example, the screen of the dewatering equipment has openings of a size from about 75 to 800 micron. And, in another example, the size of the openings range from about 150 to 500 micron.

The thin stillage from the whole stillage separation step 120 may be sent to a protein recovery step 122, which uses, for example, a decanter, a nozzle centrifuge, or a disc decanter to recover fine germ and protein (corn gluten as well as spent yeast). These recovered components are sent to a drying step 124, which utilizes a dryer, such as a rotary or ring dryer, to yield a gluten/germ mix (protein meal).

The insoluble solids (whole stillage), or the wet cake fiber portion, from the whole stillage separation step 120 is sent to a washing and dewatering step 126, which utilizes a filtration device, such as a fiber centrifuge, to separate the different fiber types by relying on a screen(s) having different sized openings. One exemplary filtration device for the wet cake washing and dewatering step 126 is shown and described in Lee U.S. Patent Application Publication No. 2010/0012596, the contents of which are incorporated herein by reference. The screen openings for the fiber centrifuge normally will be about 500 microns to capture amounts of tip cap, pericarp, as well as fine fiber, but can range from about 400 micron to about 1500 micron. Residual liquid from the centrifuge can join back up with the thin stillage prior to the protein recovery step 122. The centrifuged fiber contains less than 3% starch as compared with normal dry mill fiber, which has 4 to 6% starch in fiber. The % protein in the fiber also decreases from a conventional 29% to 21% and the % oil decreases from a conventional 9% to about 6%.

The overflow stream from the protein recovery step 122 can move to a fine protein recovery step 130, which uses, for example, a clarifier followed by a high speed decanter or disc decanter, and the like, to separate the liquid portion of the stream, which includes oil, from the remaining heavier components, including residual protein. The centrifuged protein then is sent to drying step 124, along with the recovered protein from the protein recovery step 122, to yield the gluten/germ mix (protein meal), which has about 50% protein. The total protein yield from the process is more than 4 lb./bu.

The liquid overflow from the fine protein recovery step 130 moves to evaporators in an evaporation step 136 so as to separate any oil therefrom by boiling away moisture, leaving a thick syrup. The high concentrated syrup (more than 60% DS) can be used, amongst other things, as (a) nutrition for secondary alcohol production, (b) animal feed stock, (c) plant food, (d) and/or anaerobic digestion to produce biogas. The concentrated slurry optionally can be sent to a centrifuge, for example, to separate the oil from the syrup. The oil can be sold as a separate high value product.

The syrup can be mixed with centrifuged wet cake from washing and dewatering step 126, and the mixture may be sold to beef and dairy feedlots as Distillers Wet Grain with Soluble (DWGS). The wet cake and concentrated syrup mixture also optionally may be dried in a drying step 140 and sold as Distillers Dried Grain with Soluble (DDGS) to dairy and beef feedlots. This DDGS has less than 25% protein and 8% oil.

Figure 3A:
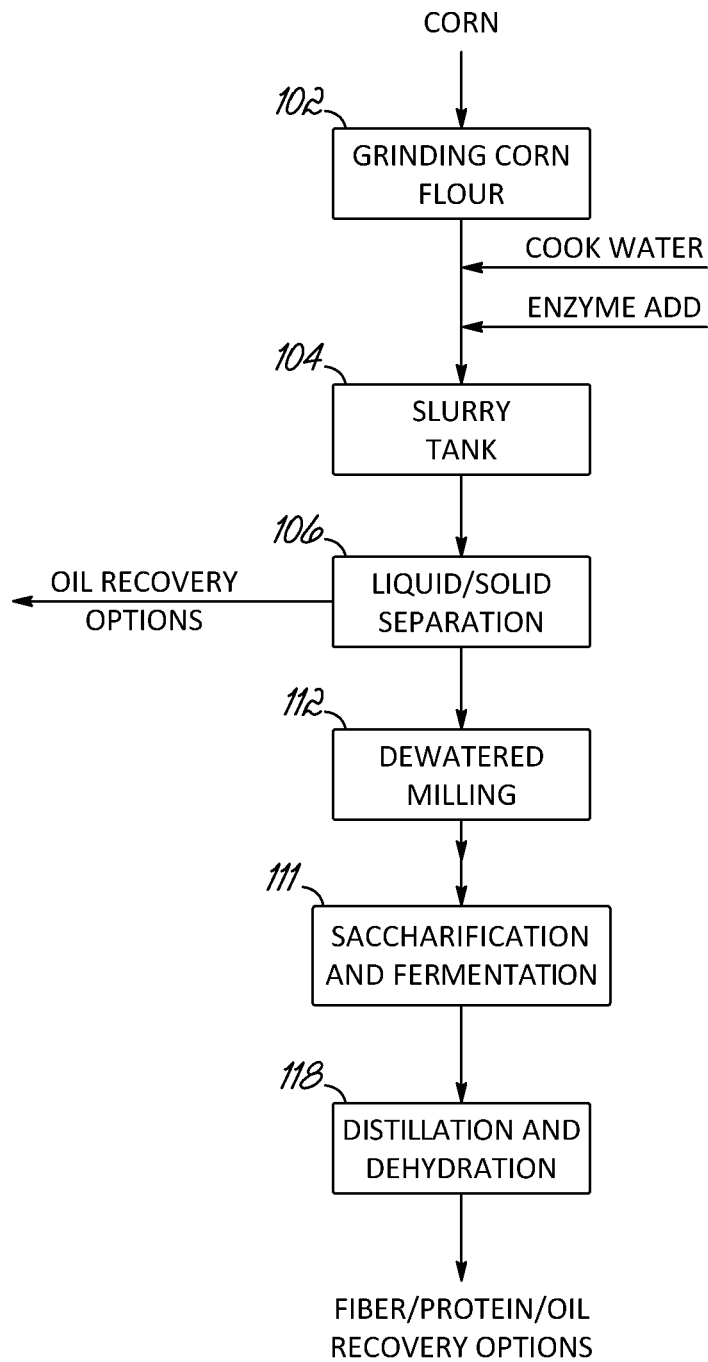
FIG. 3A is a simplified flow diagram of the dry grind ethanol production process and system of FIG. 3.

With reference now to FIG. 3A, this figure depicts a simplified flow diagram of the dry grind ethanol production process and system 100 of FIG. 3, and particularly the front end milling method, which includes in its simplest form liquid/solid separation step 106 and dewatered milling step 112. As is discussed in detail below, more than one liquid/solid separation step 106 and dewatered milling step 112 may be utilized here, for example, for alcohol, oil, protein, and/or fiber production, with desirable yields and/or purity.

With continuing reference to FIG. 3A, to accomplish this desirable alcohol, oil, protein, and/or fiber production, corn first is ground to particle sizes less than about 7/64 inch. The grinding helps break up the bonds between the fiber, protein, starch, and germ and allows for the release of oil from the corn. The ground corn flour is mixed with cook water at slurry tank 104 to create a slurry and begin liquefaction. An enzyme(s), such as alpha amylase, optionally can be added to the slurry tank 104 to assist in converting insoluble starch in the slurry to soluble starch. The stream from the slurry tank 104, which contains, e.g., sugars, protein, oil, germ particle (particle size ranges from about 50 micron to about 3 mm), grit (particle size ranges from about 50 micron to about 3 mm), and fiber (particle size ranges from about 50 micron to about 3 mm), is forwarded to the liquid/solid separation step 106. The liquid/solid separation step 106, which again defines the beginning of the front end milling method, separates a generally liquefied solution (about 60-80% by volume), which includes oil, protein, and fine solids (which do not need grinding), from heavy solids cake (about 20 to 40% by volume), which includes the heavier fiber, grit, and germ. The oil in the liquid portion optionally may be subjected to a front end oil separation step 108 to recover the free oil in the stream.

The dewatered solids portion of the stream (about 60 to 65% water) is subjected to the dewatered milling step 112, which defines the end of the front end milling method. Here, the solids, particularly the germ and grit, are reduced in size via size reduction equipment, which breaks the germ and grit particles and the bonds between fiber and starch, as well as oil and protein, without cutting the fiber too fine, thereby giving sharper separation between the fiber and protein/starch/oil. The germ and grit particles are milled to a particle size between about 300 to 800 microns, whereas a majority of the fiber remains within a particle size range of 500 to 2000 micron. Various enzymes (and types thereof) such as amylase or glucoamylase, fungal, cellulose, cellobiose, protease, and the like can be optionally added to enhance the separation of components, such as to help break the bonds between protein, starch, and fiber. The heavy slurry from the dewatered milling step 112 is subjected to pre-holding tank step 113 followed by first and second holding tanks 114 and 115 to further solubilize the starch component in the slurry stream and complete liquefaction before sending to fermentation step 111. Thereafter, alcohol and optionally fiber, oil, and/or protein are recovered from the process 100.

Figure 3B:
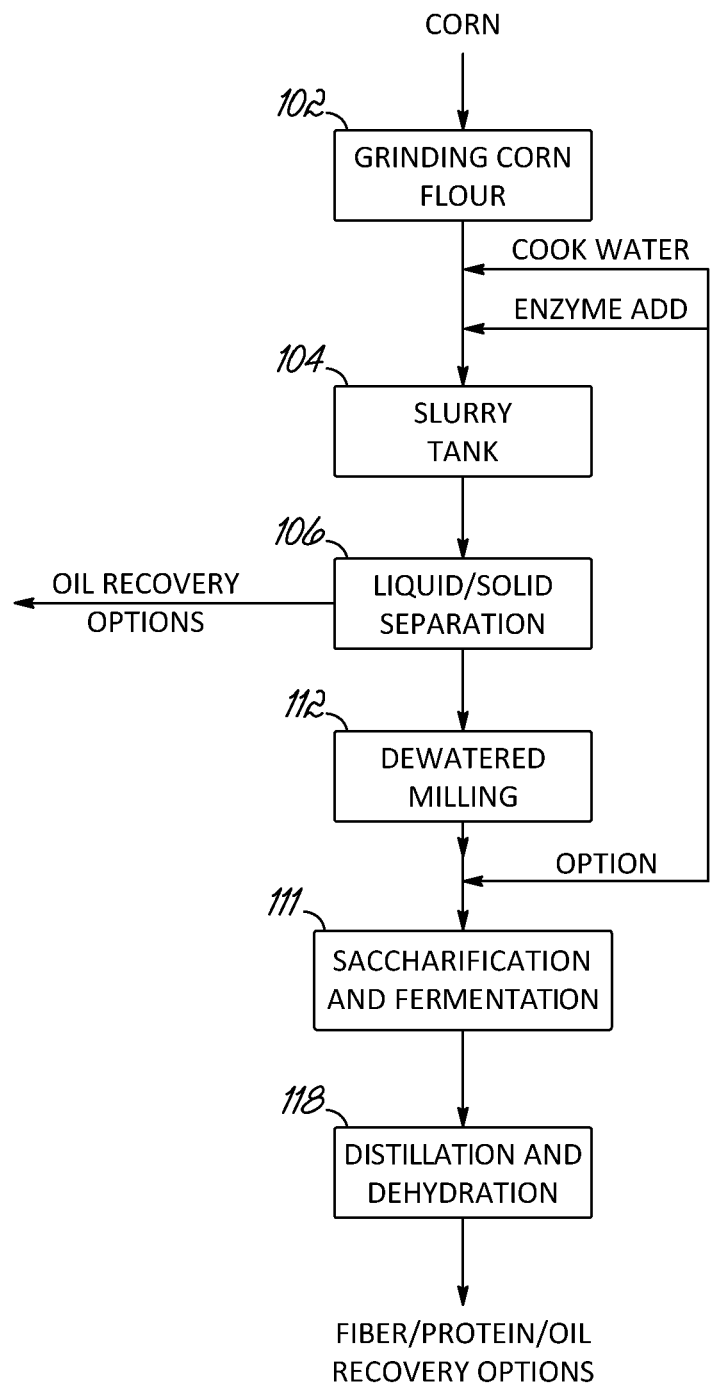
FIGS. 3B-3D are simplified flow diagrams showing a variation of the dry grind ethanol production process and system with front end milling method of FIG. 3A in accordance with embodiments of the invention.
Figure 3C:
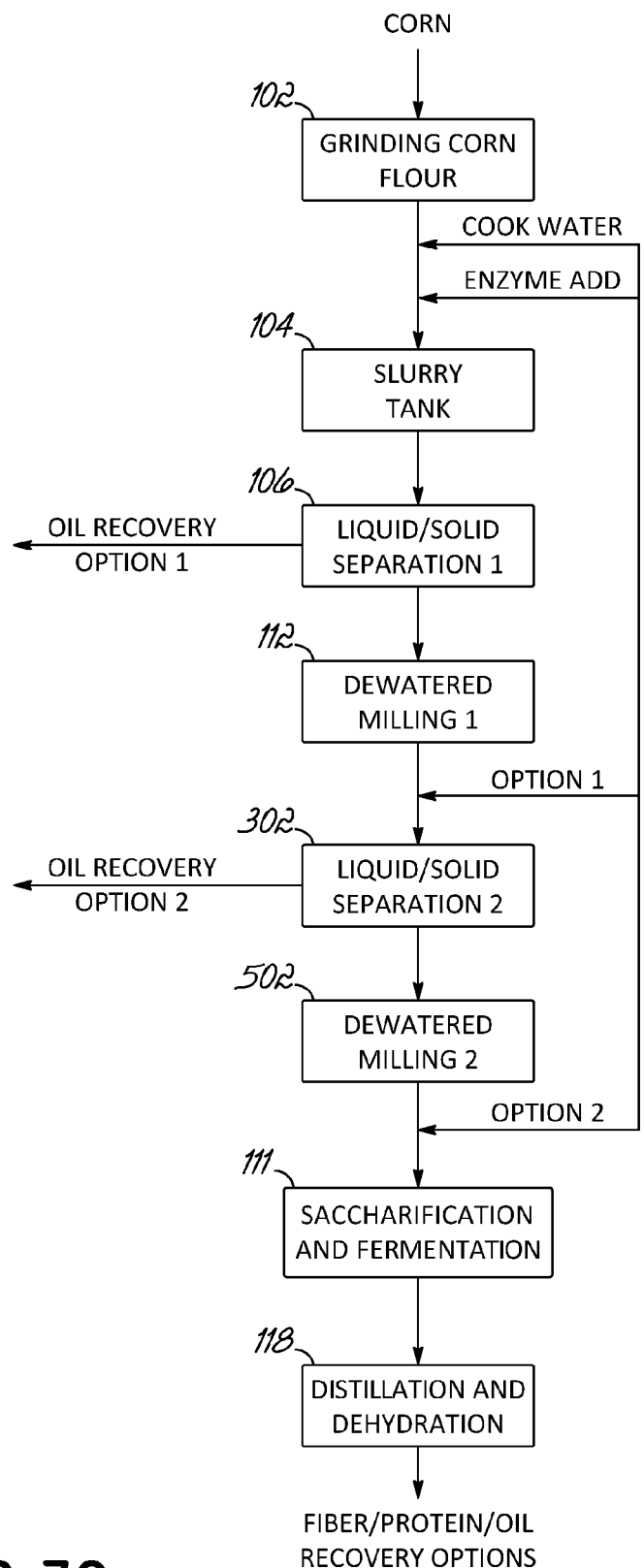
Figure 3D:
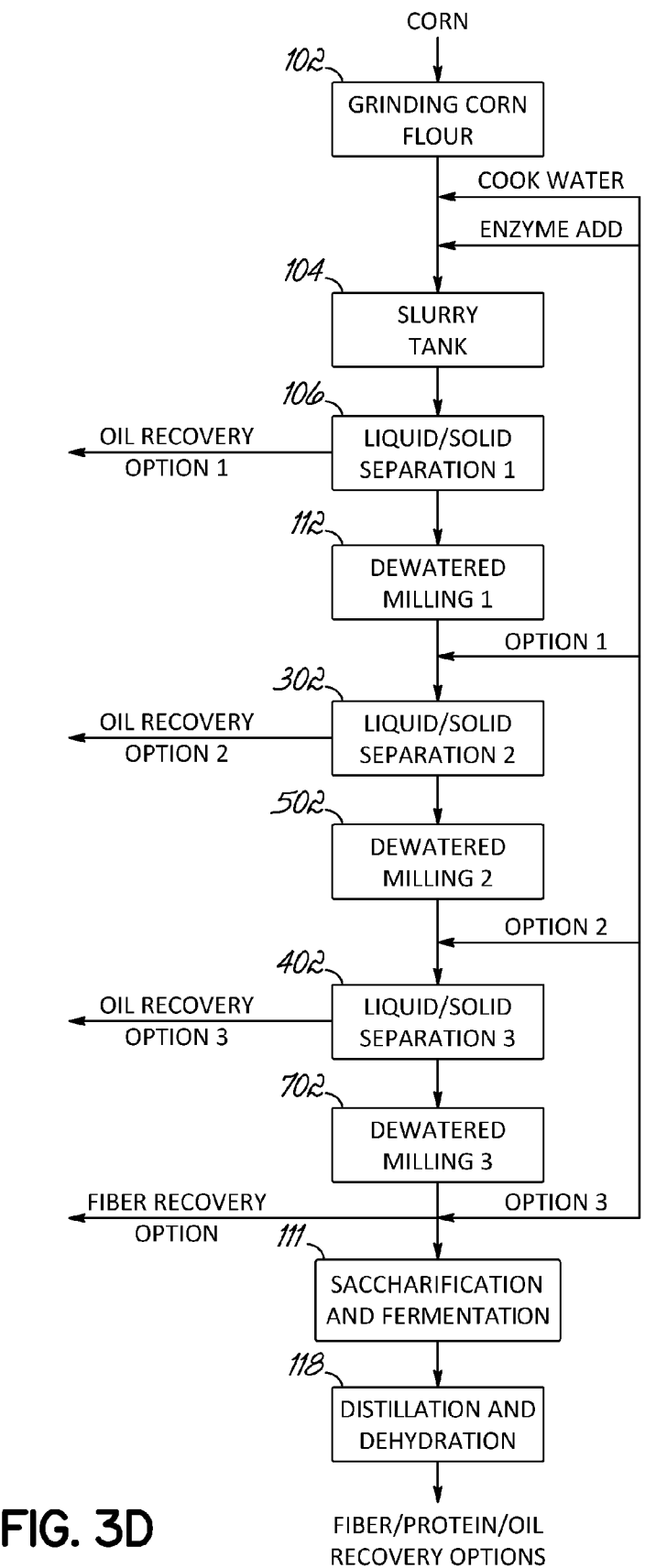

With reference now to FIGS. 3B-3D, these figures depict a simplified flow diagram showing variations of the dry grind ethanol production process and system with front end milling method of FIG. 3A in accordance with embodiments of the invention. In particular, each of FIGS. 3B-3D generally depicts optional locations of the initial cook water and optional enzyme addition, as well as the incorporation of additional optional solid/liquid separation steps 302, 402 and dewatered milling steps 502, 702. Along with the additional optional solid/liquid separations steps 302, 402, oil recovery optionally may be implemented following the additional solid/liquid separation steps 302, 402. And FIG. 3D, depicts optional front end fiber recovery. These simplified processes with their additional optional steps are discussed in greater detail below, and can be utilized for recovering alcohol, oil, protein, and/or fiber, with desirable yields and/or purity.

Figure 4:
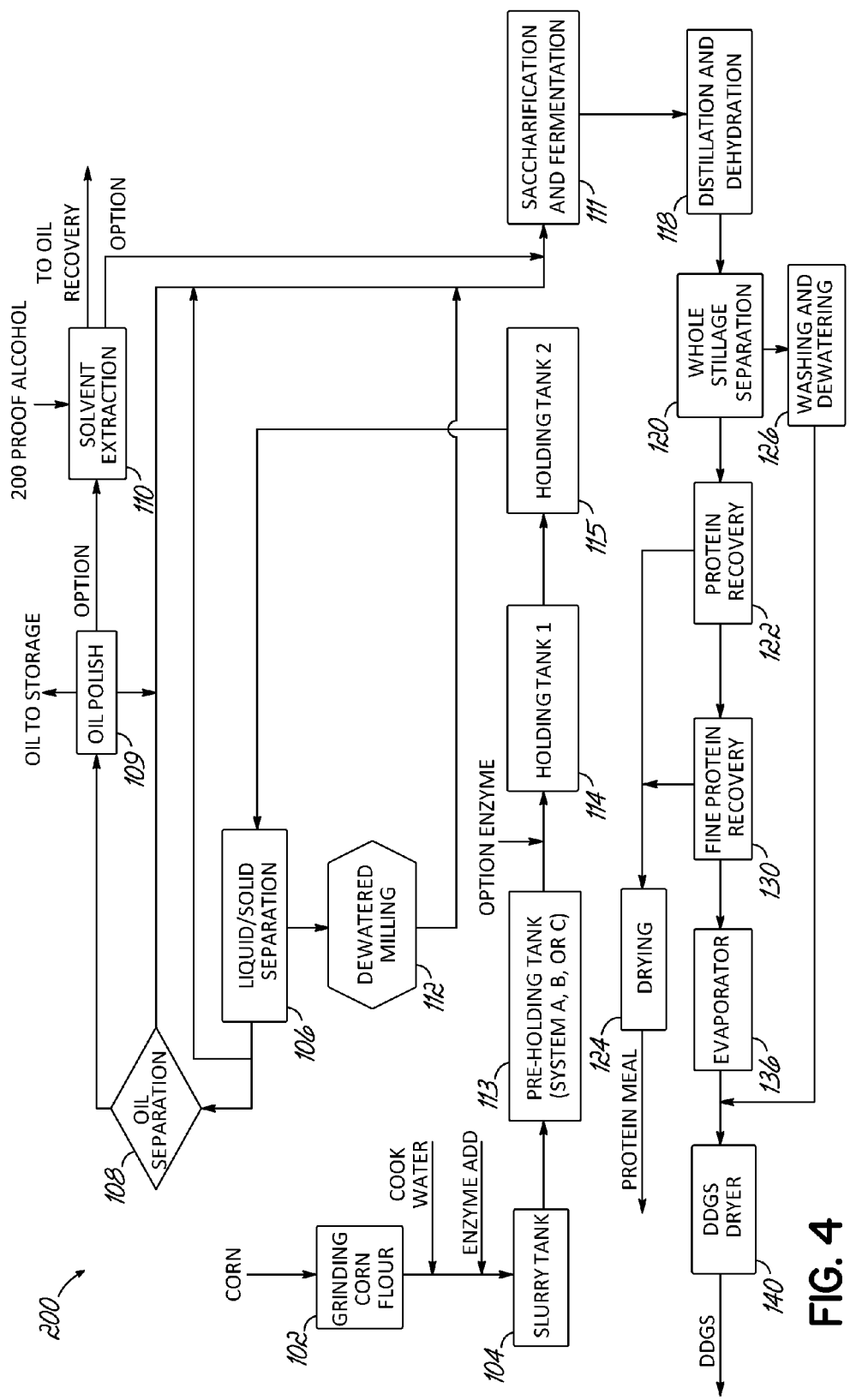
FIG. 4 is a flow diagram showing a dry grind ethanol production process and system with front end milling method in accordance with another embodiment of the invention.

With reference now to FIG. 4, this figure depicts a flow diagram of a dry grind ethanol production process and system 200 with front end milling method in accordance with another embodiment of the invention for improving alcohol and/or byproduct yields, e.g., oil and/or protein yields. To an extent, this process 200 is a variation of the dry grind ethanol production process 100 with front end milling method of FIG. 3. Here, in FIG. 4, the front end milling method, which includes the liquid/solid separation step 106 and the dewatered milling step 112, is situated after the second holding tank 115 and before fermentation step 111, as a way to increase oil recovery, rather than after the slurry tank 104. As a result, the feed that is sent to the oil separation step 108 has a lower viscosity and a higher Brix, which is understood to make oil recovery more efficient. In contrast, the process 100 of FIG. 3 is understood to increase alcohol yield by enabling a greater release of starch.

Due to the location of the front end milling method, as shown in FIG. 4, the feed from the slurry tank 104 is sent directly to the pre-holding tank step 113 (instead of to the liquid/solid separation step 106 as shown in FIG. 3), whereat the slurry is subjected to one of systems A, B, or C, as discussed above. Thereafter, the slurry is sent to the first and second holding tanks 114 and 115 to further solubilize the starch component in the slurry stream.

The slurry stream from the second holding tank 115 is next subjected to the liquid/solid separation step 106, which defines the beginning of the front end milling method. The liquid/solid separation step 106 again separates the liquefied solution (about 65-85% by volume), which includes oil, protein, and fine solids (which do not need grinding), from the heavy solids cake (about 15 to 35% by volume), which includes the heavier fiber, grit, and germ. The now separated liquefied starch solution can move to the optional oil separation step 108, to separate oil from the liquefied starch solution by taking advantage of density differences, and an oil/emulsion/germ layer can be further forwarded to the oil polish step 109.

The dewatered solids portion of the stream at the liquid/solid separation step 106 (about 60 to 65% water) continues along the front end milling method and is next subjected to the dewatered milling step 112, whereat the solids, particularly the germ and grit, are reduced in size via size reduction equipment. After milling, which defines the end of the front end milling method, the solids are mixed with the liquefied starch solution from either the optional oil separation step 108 or from the liquid/solid separation step 106 to form a heavy slurry and subjected to the fermentation step 111. Also, if the emulsion and fine germ particle from the oil polish step 109 are not optionally subjected to the solvent extraction step 110, the underflow (mainly liquefied starch) is joined up with the underflow solution from the oil separation step 108, which is joined up with the solids from the dewatered milling step 112 to form the heavy slurry, and sent to the fermentation step 111. The rest of the dry grind ethanol production process 200 is generally the same as that of FIG. 3.

While not intending to be limiting, it should be further understood that the front end milling method also can be utilized between the pre-holding tank step 113 and the first holding tank 114, or the first holding tank 114 and the second holding tank 115, and the like, for example.

Figure 5:
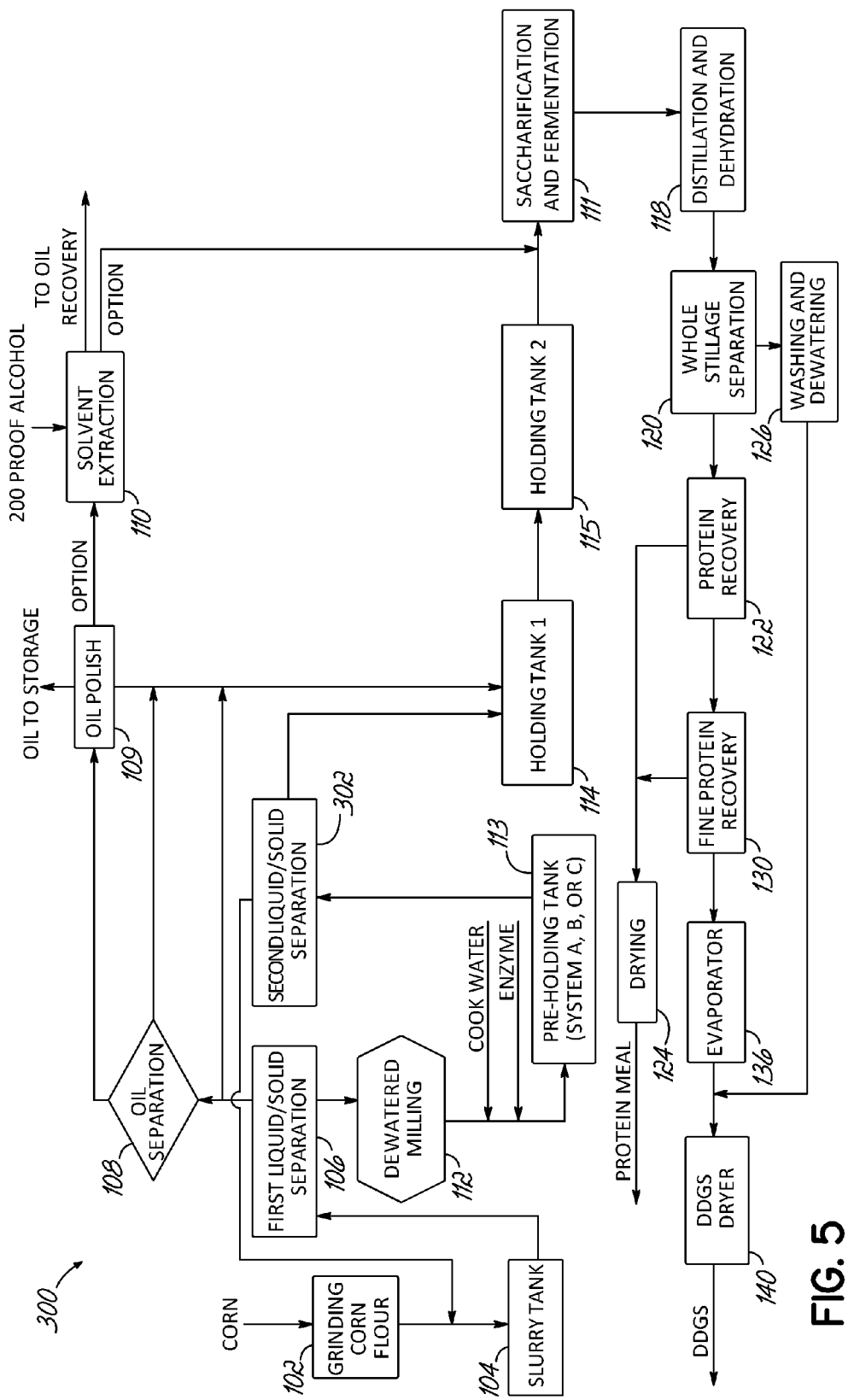
FIG. 5 is a flow diagram showing a dry grind ethanol production process and system with front end milling method in accordance with another embodiment of the invention.

With reference now to FIG. 5, this figure depicts a flow diagram of a dry grind ethanol production process and system 300 with front end milling method in accordance with another embodiment of the invention for improving alcohol and/or byproduct yields, e.g., oil and/or protein yields. To an extent, this process 300 is a variation of the dry grind ethanol production process 100 with front end milling method of FIG. 3. In this process 300, at the front end, as compared to the process 100 of FIG. 3, there is an additional liquid/solid separation step 302, which is situated between the pre-holding tank step 113 and the first holding tank 114 and is considered as an addition to the front end milling method. In an effort to maximize alcohol, protein, and/or oil yield, counter current washing also is set-up in this process 300 where filtrate, which includes liquefied starch plus middle size solids, is removed from the slurry stream at the second liquid/solid separation step 302. This filtrate is recycled back to mix with the ground corn flour just prior to slurry tank 104 to create a slurry and begin liquefaction, and replaces the initial cook water that is used in the embodiment shown in FIG. 3. As such, cook water now is initially added after the dewatered milling step 112, as compared to just after the grinding step 102, in the process 300 of FIG. 5. This counter current washing set-up allows additional liquefied starch and middle size solids to be recycled back to the dewatered milling step 112 one or more times, without the need for additional dewatered milling equipment. The recycled liquefied starch re-visits the first liquid/solid separation step 106 whereat it can be separated out by traveling through the screen, then may be sent to the first holding tank 114.

With continuing reference now to FIG. 5, the feed from the slurry tank 104 is subjected to the first liquid/solid separation step 106, which defines the beginning of the front end milling method. The liquid/solid separation step 106 again separates the liquefied solution (about 60-80% by volume), which includes oil, protein, and fine solids (which do not need grinding), from the heavy solids cake (about 20 to 40% by volume), which includes the heavier fiber, grit, and germ. The now separated liquefied starch solution can move to the optional oil separation step 108, to separate oil from the liquefied starch solution by taking advantage of density differences, and then oil/emulsion/germ layer can be further forwarded to the oil polish step 109.

The dewatered solids portion of the stream at the liquid/solid separation step 106 (about 60 to 65% water) continues along the front end milling method and is next subjected to the dewatered milling step 112, whereat the solids, particularly the germ and grit, are reduced in size via size reduction equipment. After milling, the solids are mixed with the cook water to form a heavy slurry and subjected to one of three optional pre-holding tank systems at pre-holding tank step 113, i.e., generally one of systems A, B, and C of FIG. 2. The addition of cook water after the dewatered milling step 112 helps with washing out and separating liquefied starch, oil, and middle size solids.

The slurry from the pre-holding tank step 113 next is forwarded to the second liquid/solid separation step 302. And as with the first liquid/solid separation step 106, the second liquid/solid separation step 302 uses dewatering equipment, e.g., a paddle screen, a vibration screen, a filtration, scroll screen, or conic screen centrifuge, a pressure screen, a pre-concentrator, and the like, to accomplish separation of the solids from the liquid portion. In one example, the dewatering equipment is a paddle screen or a preconcentrator, as above described. With the second liquid/solid separation step 302, the actual screen openings may be larger in size than those in the first liquid/solid separation step 106, which can provide higher alcohol and oil yield. In one example, the screen size used in the first liquid/solid separation step 106 can range from 45 micron to 300 micron, and the screen size used in the second liquid/solid separation step 302 can range from about 300 to 800 micron size. The filtrate, which is removed from the second liquid/solid separating step 302 and joined up with the ground corn flour prior to the slurry tank 104, contains about 6 to 10 Brix liquefied starch solution as well as solid particles (germ, grit, and protein) having sizes smaller than the screen size openings used in the second liquid/solid separation step 302. Using a smaller screen at the first liquid/solid separation step 106 and a larger screen at the second liquid/solid separation step 302, the counter-current setup allows one to target grinding of grit and germ particles greater than the screen size at the first liquid/solid separation step 106 and smaller than the screen size at the second liquid/solid separation step 302. Particles larger than the screen size at the second liquid/solid separation step 302 tend to be mostly fiber and contain less starch, so they do not need to recycle for additional milling at the dewatered milling step 112.

The dewatered solids portion of the stream is next forwarded, in series, to first and second holding tanks 114 and 115 for a total holding time of about 2 to 4 hours at temperatures of about 66° C. to 85° C. to further solubilize the starch component in the slurry stream and complete liquefaction before sending to fermentation step 111. In this process 300, the liquefied starch solution from the optional oil separation step 108 and optionally the emulsion and fine germ particle from the oil polish step 109 can be joined up with the heavy solids from the second liquid/solid separation step 302 at the first holding tank 114. Also, the liquefied starch solution from the first liquid/solid separation step 106 may be combined with the solids here at the first holding tank 114 if the optional oil separation step 108 is not utilized. The rest of the dry grind ethanol production process 300 is generally the same as that of FIG. 3.

The counter current washing set up in this process 300 is understood to create a desirable way to control the temperature, brix, pH, and enzyme concentration profile of the slurry throughout the liquefaction process, i.e., from the slurry tank 104 to the second holding tank 115. For example, when the cook water and fresh enzyme, as shown in FIG. 5, are added near the back end of liquefaction and subjected to the first and second holding tank steps 114, 115, the conditions of the slurry (e.g., pH, temperature, and Brix) can be controlled by adjusting the amount of cook water and the source of the cook water, which normally includes fresh cool well water and hot condensate from the evaporator and $CO_2$ scrubber. These cook water sources, which have different temperatures, pH, etc., can be manipulated to provide optimum results for the liquefaction process, including helping to minimize the formation of nonconvertible starch, and to minimize retrograded starch during saccharification.

In addition, the combination of the first and second liquid/solid separation steps 106, 302 and the dewatered milling step 112 helps provide an additional increased yield of 1.5% alcohol, about 0.1 lb/bu more oil, and 0.5 lb/bu more protein. And the amount of back washing water for counter current washing is only a portion of the total cook water flow, e.g., about 50%. As such, the heavy cake content in the slurry that is subjected to the first and second holding tanks 114, 115 approximately doubles, which in turn doubles the average holding time that is necessary to give a more complete liquefaction, for example.

Figure 6:
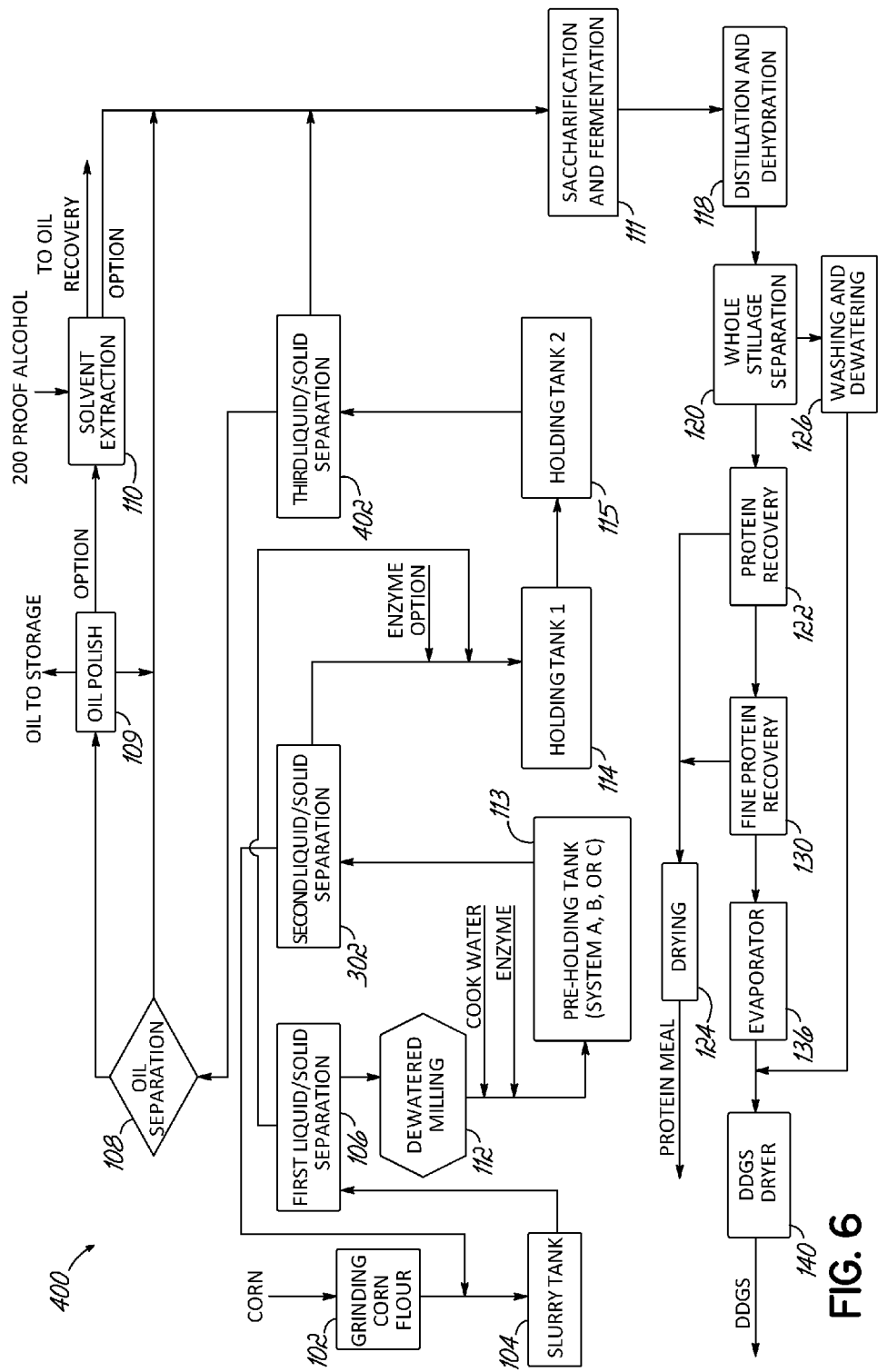
FIG. 6 is a flow diagram showing a dry grind ethanol production process and system with front end milling method in accordance with another embodiment of the invention.

With reference now to FIG. 6, this figure depicts a flow diagram of a dry grind ethanol production process and system 400 with front end milling method in accordance with another embodiment of the invention for improving alcohol and/or byproduct yields, e.g., oil and/or protein yields. To an extent, this process 400 is a variation of the dry grind ethanol production process 300 with front end milling method of FIG. 5. Here, in FIG. 6, at the front end of the process 400, as compared to the process 300 of FIG. 5, there is a third liquid/solid separation step 402, which is situated between the second holding tank 115 and fermentation step 111, and is considered as an addition to the front end milling method.

As shown in FIG. 6, the feed from the slurry tank 104 is subjected to the first liquid/solid separation step 106, which defines the beginning of the front end milling method. The first liquid/solid separation step 106 again separates the liquefied solution (about 60-80% by volume), which includes oil, protein, and fine solids (which do not need grinding), from the heavy solids cake (about 20 to 40% by volume), which includes the heavier fiber, grit, and germ. Rather than move to the optional oil separation step 108 as shown in FIG. 5, the now separated liquefied starch solution is forwarded to join up with the dewatered solids from the second liquid/solid separation step 302. Next, these dewatered solids are subjected to the first followed by the second holding tanks 114, 115 for a total holding time of about 2 to 4 hours at temperatures of about 66° C. to 85° C. to further solubilize the starch component in the slurry stream before sending the slurry to the third liquid/solid separation step 402. Various enzymes (and types thereof) such as amylase or glucoamylase, fungal, cellulose, cellobiose, protease, and the like can be optionally added to the dewatered solids from the second liquid/solid separation step 302 prior to the first holding tank 114 to enhance the separation of components, such as to help break the bonds between protein, starch, and fiber.

As with the first and second liquid/solid separation steps 106 and 302, the third liquid/solid separation step 402 uses dewatering equipment, e.g., a paddle screen, a vibration screen, a filtration, scroll screen, or conic screen centrifuge, a pressure screen, a pre-concentrator, and the like, to accomplish separation of the solids from the liquid portion. In one example, the dewatering equipment is a paddle screen or a pre-concentrator, as above described. With the second liquid/solid separation step 302, the actual screen openings may be larger in size than those in the first and/or third liquid/solid separation steps 106, 402.

At the third liquid/solid separation step 402, the liquefied solution (about 70-85% by volume), which includes oil, protein, and fine solids, is separated from the heavy solids cake (about 15-30% by volume), which includes the heavier fiber, grit, and germ. The now separated liquefied starch solution can move to the oil separation step 108, to separate oil from the liquefied starch solution by taking advantage of density differences, and an oil/emulsion/germ layer can be further forwarded to the oil polish step 109. If the oil recovery centrifuge in the oil separation step 108 is specifically a three phase decanter, the third liquid/solid separation step 402 may be eliminated. However, the three phase decanter performance can be improved by retaining the third liquid/solid separation step 402.

With further reference to FIG. 6, the underflow heavy phase and solid phase from the third liquid/solid separation step 402 can be combined and forwarded on to join up with the liquefied starch solution from the oil separation step 108, and optionally the emulsion and fine germ particle from the oil polish step 109 and the remaining fine germ particle from the solvent extraction step 110, then directly subjected to fermentation 111. Although not depicted in FIG. 6, if the oil separation step 108 is not optionally utilized here, the third liquid/solid separation step 402 may be eliminated and the liquefied starch slurry solution sent directly from the second holding tank 115 to fermentation step 111. The rest of the dry grind ethanol production process 300 is generally the same as that of FIG. 5.

Although not illustrated, it should be understood that the processes 300 and 400 of FIG. 5 and FIG. 6, respectively, can be re-arranged so that the feed that goes to the oil separation step 108, for example, can be sent from the pre-holding tank step 113, the first holding tank 114, or the like. With respect to increasing alcohol yield, the process 300 in FIG. 5 is understood to be desirable for releasing more starch, whereas the process 400 in FIG. 6 is understood to be more desirable for oil recovery because the feed for the oil separation step 108 of FIG. 6 will have lower viscosity and higher Brix.

Figure 7:
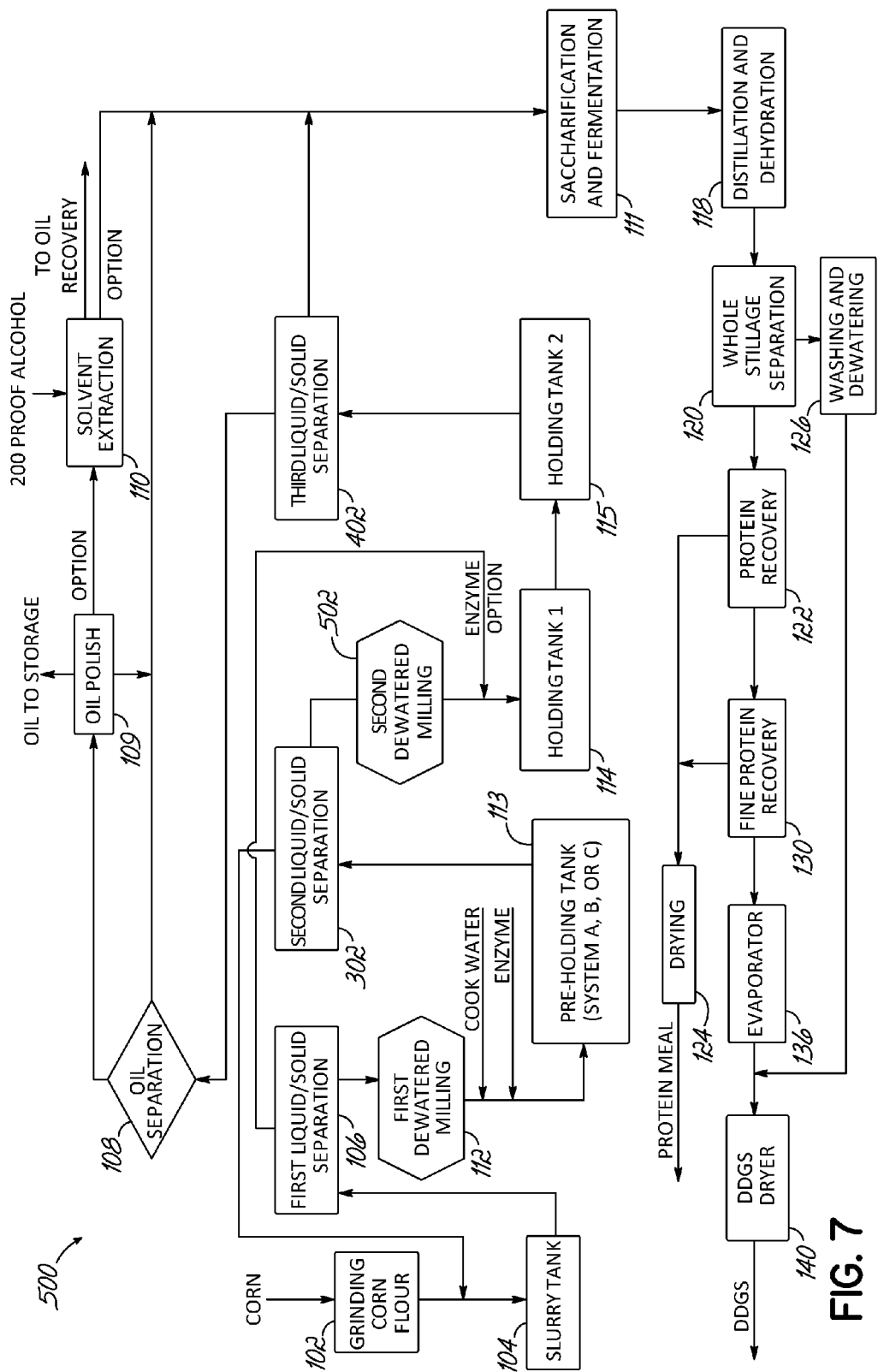
FIG. 7 is a flow diagram showing a dry grind ethanol production process and system with front end milling method in accordance with another embodiment of the invention.

With reference now to FIG. 7, this figure depicts a flow diagram of a dry grind ethanol production process and system 500 with front end milling method in accordance with another embodiment of the invention for improving alcohol and/or byproduct yields, e.g., oil and/or protein yields. To an extent, this process 500 is a variation of the dry grind ethanol production process 400 with front end milling method of FIG. 6. Here, in FIG. 7, at the front end of the process 500, as compared to the process 400 of FIG. 6, there is added a second dewatered milling step 502, which is situated between the second liquid/solid separation step 302 and first holding tank 114, and is considered as an addition to the front end milling method. Thus, with this process 500, there is provided three liquid/solid separation steps 106, 302, 402, and two dewatered milling steps 112 and 502 in the front end milling method. It is noted that to release starch from germ and grit particles, the particle size should be smaller than about 300 to 400 micron, whereas to release oil from germ particles, the particle size should be smaller than about 75 to 150 micron. To increase alcohol yield, while two dewatered milling steps 112, 502 in a series are desirable, one will suffice. Yet, to increase oil yield, two dewatered milling steps 112, 502 are desirable.

With continuing reference to FIG. 7, the dewatered solids portion of the stream at the second liquid/solid separation step 302 continues along the front end milling method and is subjected to the second dewatered milling step 502, whereat the solids, particularly the germ and grit, are further reduced in size via size reduction equipment. The size reduction equipment can include a hammer mill, a pin or impact mill, a grind mill, and the like. In one example, the size reduction equipment is a pin mill or grind mill. This second dewatered milling step 502 is intended to further break the germ and grit particles and the bonds between fiber and starch, as well as oil and protein, without cutting the fiber too fine, thereby giving sharper separation between the fiber and protein/starch/oil. In a dewatered form, the germ and grit particles are able to break apart more easily than the fiber as a result of increased rubbing action in which less fine fiber is created, but the germ and grit are more fully milled. This results in a relatively non-uniform particle size amongst the milled solids. For example, germ and grit particles can be milled here to particle sizes between about 75 to 150 microns, whereas a majority of the fiber remains within a particle size range of 300 to 800 micron. In one example, greater than 75% of the fiber remains within a particle size range of 300 to 1000 micron. In another example, about 30% to about 60% by weight of the total particles after the second dewatered milling step 502 have a particle size from about 100 microns to about 800 microns. In still another example, about 40% to about 50% by weight of the total particles after the second dewatered milling step 502 have a particle size from about 100 microns to about 800 microns. In yet another example, no greater than 60% by weight of the total particles after the second dewatered milling step 502 have a particle size from about 100 microns to about 800 microns. In yet another example, no greater than 50% by weight of the total particles after the second dewatered milling step 502 have a particle size from about 100 microns to about 800 microns. The rest of the dry grind ethanol production process 500 is generally the same as that of FIG. 6.

The combination of the three liquid/solid separation steps 106, 302, 402, and two dewatered milling steps 112 and 502 in the front end milling method of FIG. 7 helps provide an additional increased yield of 2% alcohol, about 0.15 lb/bu more oil, and 0.8 lb/bu more protein.

Figure 7A:
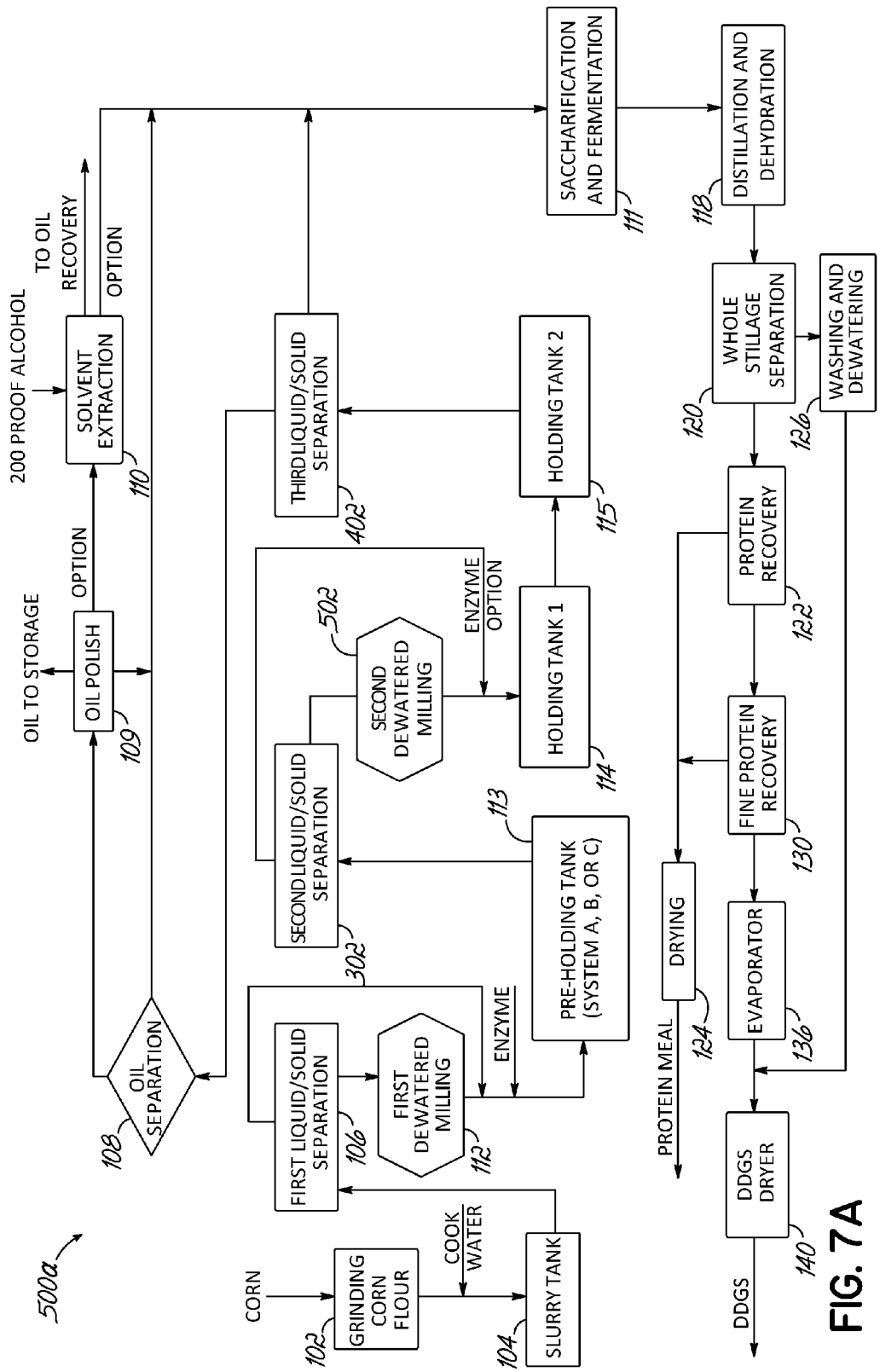
FIG. 7A is a flow diagram showing a variation of the dry grind ethanol production process and system with front end milling method of FIG. 7 in accordance with an embodiment of the invention.

With reference now to FIG. 7A, this figure depicts a flow diagram showing a variation of the dry grind ethanol production process and system 500 with front end milling method of FIG. 7 in accordance with another embodiment of the invention for improving alcohol and/or byproduct yields, e.g., oil and/or protein yields. In this process 500A, the counter current washing of FIG. 7, which includes removing and recycling back the liquefied starch plus middle size solids from the slurry stream at the second liquid/solid separation step 302 so as to mix with the ground corn flour just prior to slurry tank 104, is eliminated. Instead, the ground corn flour is again mixed with initial cook water at the slurry tank 104 to create a slurry and begin liquefaction, as in FIG. 3. In turn, the filtrate from the second liquid/solid separation step 302 is joined up with the milled solids from the second dewatered milling step 502 rather than the separated liquefied solution from the first liquid/solid separation step 106. Also, the liquefied solution from the first liquid/solid separation step 106 is similarly joined up with the milled solids from the first dewatered milling step 112. And the rest of the dry grind ethanol production process 500A is generally the same as that of FIG. 7.

Figure 7B:
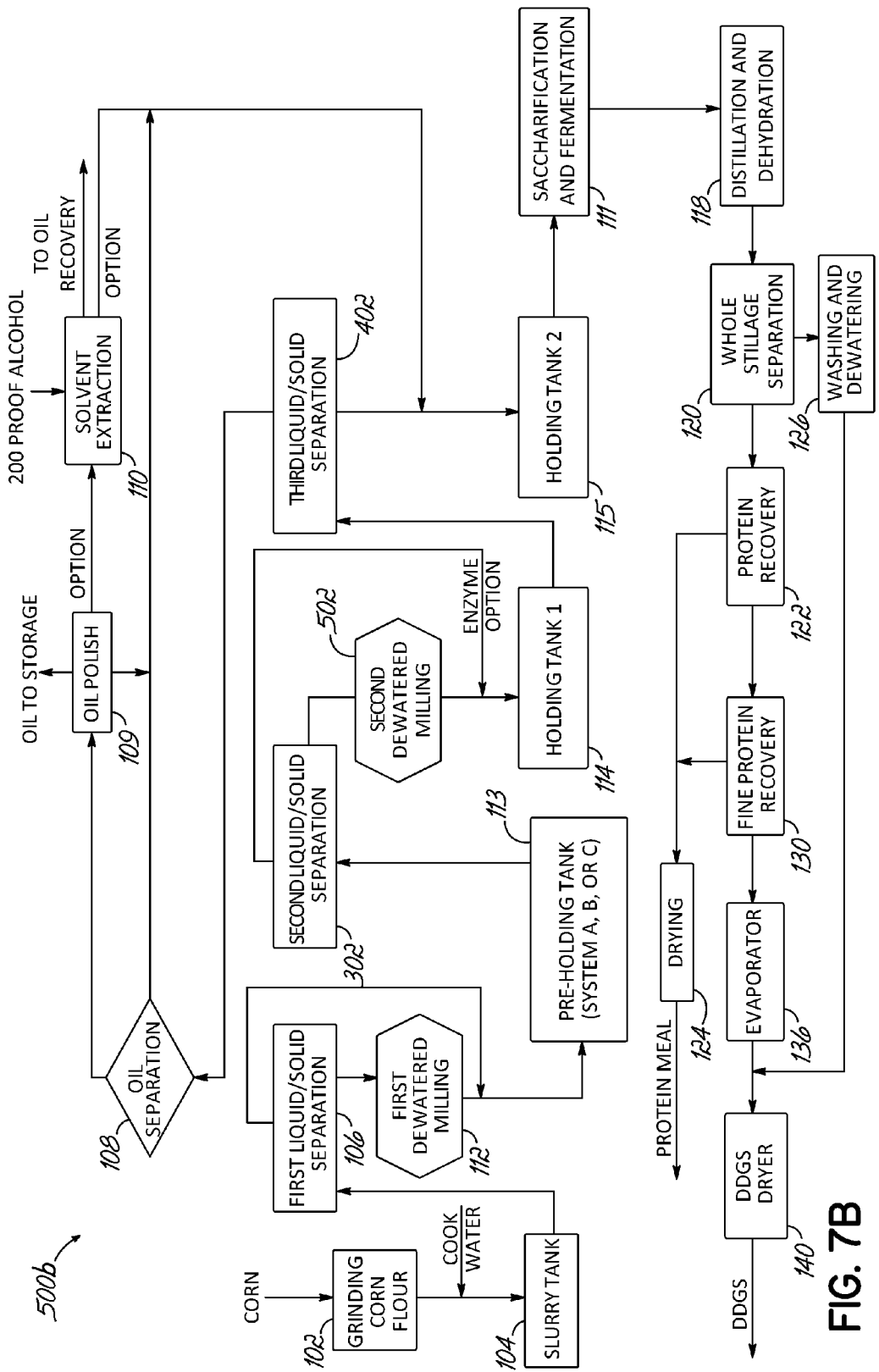
FIG. 7B is a flow diagram showing a variation of the dry grind ethanol production process and system with front end milling method of FIG. 7A in accordance with an embodiment of the invention.

With reference now to FIG. 7B, this figure depicts a flow diagram showing a variation of the dry grind ethanol production process and system 500A with front end milling method of FIG. 7A in accordance with another embodiment of the invention for improving alcohol and/or byproduct yields, e.g., oil and/or protein yields. Rather than subjecting the slurry formed from the filtrate from the second liquid/solid separation step 302 and the milled solids from the second dewatered milling step 502 to the first followed by the second holding tanks 114, 115, the slurry from the first holding tank 114 is subjected to the third liquid/solid separation step 402. Again, the third liquid/solid separation step 402 uses dewatering equipment to accomplish separation of the solids from the liquid portion. The liquefied solution (about 70-85% by volume), which includes oil, protein, and fine solids, is separated from the heavy solids cake (about 15-30% by volume), which includes the heavier fiber, grit, and germ.

The now separated liquefied starch solution can move to the optional oil separation step 108, and the underflow heavy phase and solid phase can be forwarded on to join up with the liquefied starch solution from the optional oil separation step 108, and optionally the emulsion and fine germ particle from the oil polish step 109 and the remaining fine germ particle from the solvent extraction step 110, then subjected to the second holding tank 115. Thereafter, the slurry is sent to and subjected to the fermentation step 111. The total holding time in the first and second holding tanks is about 2 to 4 hours at temperatures of about 66° C. to 85° C. to further solubilize the starch component in the slurry stream and complete liquefaction before sending to fermentation step 111. The rest of the dry grind ethanol production process 500B is generally the same as that of FIG. 7A.

Figure 8:
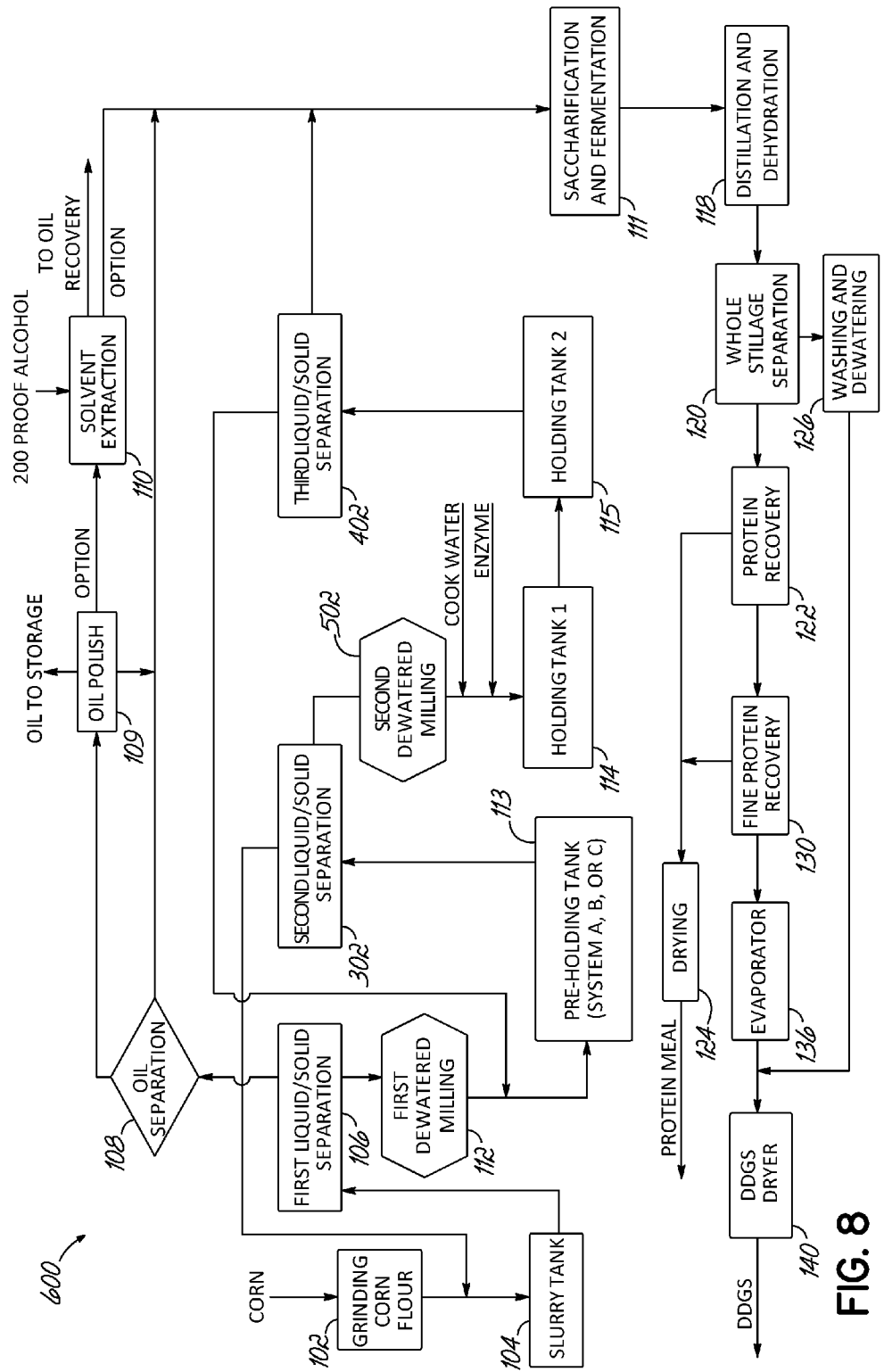
FIG. 8 is a flow diagram showing a dry grind ethanol production process and system with front end milling method in accordance with another embodiment of the invention.

With reference now to FIG. 8, this figure depicts a flow diagram of a dry grind ethanol production process and system 600 with front end milling method in accordance with another embodiment of the invention for improving alcohol and/or byproduct yields, e.g., oil and/or protein yields. To an extent, this process 600 is a variation of the dry grind ethanol production process 500 with front end milling method of FIG. 7. Here, in FIG. 8, at the front end of the process 600, as compared to the process 500 of FIG. 7, the liquefied solution (about 60-80% by volume) from the first liquid/solid separation step 106 is sent to the oil separation step 108 (and an oil/emulsion/germ layer can be further forwarded to the oil polish step 109), rather than forwarded to join the milled solids after the second dewatered milling step 502. The dewatered solids portion of the stream at the first liquid/solid separation step 106 (about 60 to 65% water) continues along the front end milling method and is next subjected to the first dewatered milling step 112, whereat the solids are reduced in size via size reduction equipment.

To that end and in a further effort to maximize alcohol, protein, and/or oil yield, additional counter current washing is set-up in this process 600 where filtrate, which includes liquefied starch plus middle size solids (2 to 6 Brix of liquefied starch solution), is removed from the slurry stream at the third liquid/solid separation step 402. This filtrate, similar to the filtrate from the second liquid/solid separation step 302, is recycled back to mix with the milled solids after the first dewatered milling step 112. The heavy slurry then is subjected to one of three optional pre-holding tank systems at pre-holding tank step 113, i.e., generally one of systems A, B, and C of FIG. 2, whereat the slurry is held for about 0.5 to 1 hour holding time before being sent on to the second liquid/solid separation step 302. The recycled filtrate from the third liquid/solid separation step 402 replaces the cook water that is used in the process 500 of FIG. 7, which combines with the milled solids after first dewatered milling step 112. In view thereof, the cook water in the process 600 is now initially added after the second dewatered milling step 112, along with optional enzymes, as previously discussed. The counter current wash set-up allows for released oil and smaller starch/converted sugar particles to travel through the screens and wash forward again as larger starch particles and grit continue to wash downstream for additional grinding and treatment prior to fermentation. Oil recovery is understood to be successful because of the high concentration of sugars and oil recycling back to the initial slurry, which mixes with the initial free oil for later recovery. Although not depicted in FIG. 8, if the oil separation step 108 is not optionally utilized here, the liquefied starch solution from the first liquid/solid separation step 106 can be joined up with the solids portion from the third liquid/solid separation step 402 and sent directly to fermentation step 111. The rest of the dry grind ethanol production process 600 is generally the same as that of FIG. 7.

With continuing reference to FIG. 8, the screen size for the liquid/solid separation steps 106, 302, 402 can be selected so that certain size solid particles will be recycled back to one or more of the dewatered milling steps 112, 502 so as to be subjected to further grinding. For example, a 75 micron screen size may be utilized in the first liquid/solid separation step 106, a 150 micron screen size in the second liquid/solid separation step 302, and a 300 micron screen size in the third liquid/solid separation step 402. With the counter current washing set up, the grit and germ particle can be selectively ground to desired particle sizes. In one example, the grit size should be less than about 300 micron for increased alcohol yields. In another example, the germ size should be less than about 150 micron for increased oil yields increase. In another example, the germ size should be less than 45 micron for increased oil yields increase. The combination of the first, second, and third liquid/solid separation steps 106, 302, and 402 and the first and second dewatered milling steps 112 and 502 arranged in this counter current wash setup helps provide an additional increased yield of 2% alcohol, about 0.15 lb/bu more oil, and 0.8 lb/bu more protein.

Figure 9:
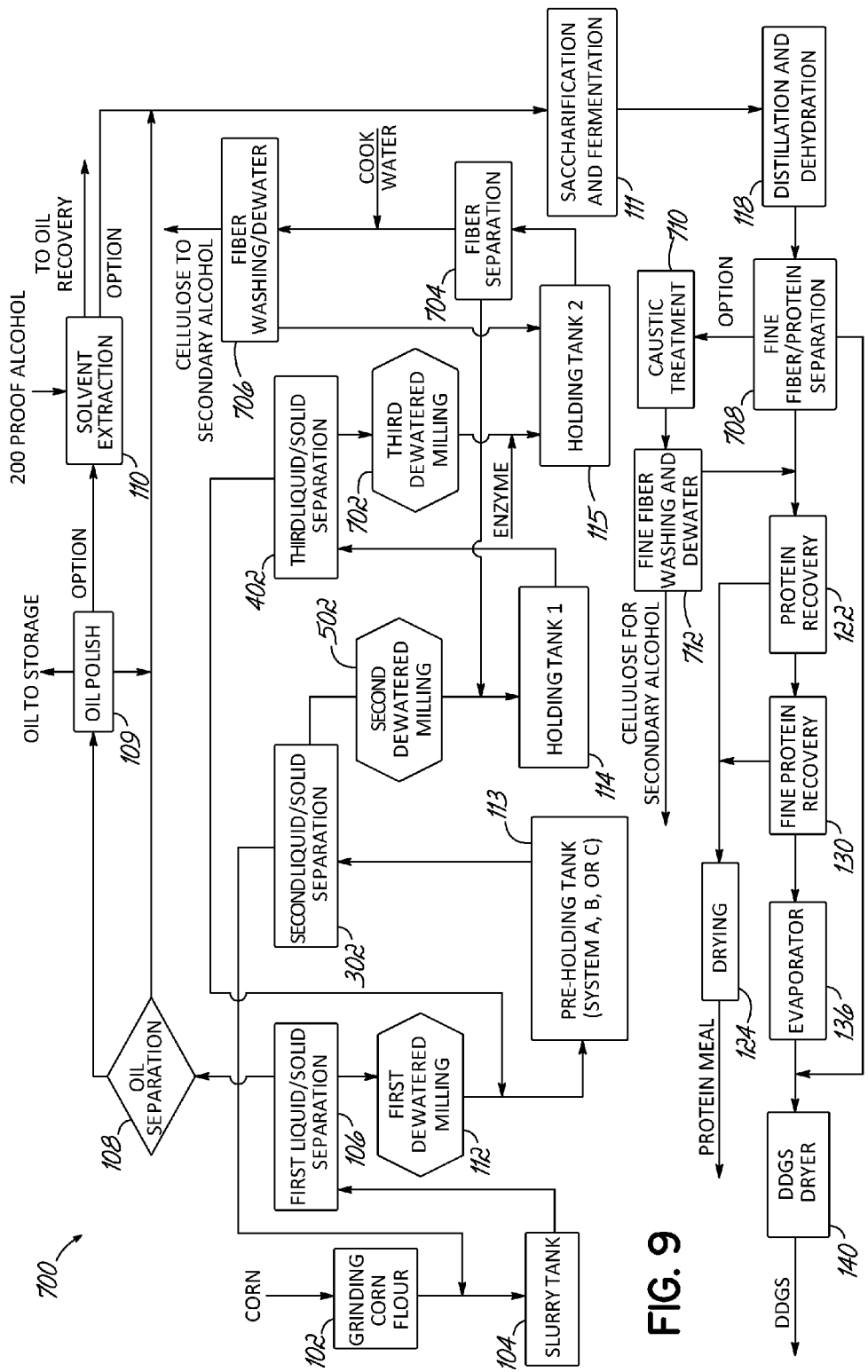
FIG. 9 is a flow diagram showing a dry grind ethanol production process and system with front end milling method in accordance with another embodiment of the invention.

With reference now to FIG. 9, this figure depicts a flow diagram of another embodiment of a dry grind ethanol production process and system 700 with front end milling method for improving alcohol and/or byproduct yields, e.g., oil and/or protein yields. To an extent, this process 700 is a variation of the dry grind ethanol production process 600 with front end milling method of FIG. 8. Here, in FIG. 9, at the front end of the process 700, as compared to the process 600 of FIG. 8, there is a third dewatered milling step 702, which is situated between the third liquid/solid separation step 402 and the second holding tank 115, and is considered as an addition to the front end milling method. In addition, rather than subjecting the milled solids from the second dewatered milling step 502 to the first followed by the second holding tanks 114, 115, the slurry from the first holding tank 114 is first subjected to the third liquid/solid separation step 402 to accomplish separation of the solids from the liquid portion. Also, filtrate from a fiber separation step 704, similar to the filtrate from the second liquid/solid separation step 302, is recycled back in a counter current set up to mix with milled solids after the second dewatered milling step 502 to form a heavy slurry. This heavy slurry is sent to the first holding tank 114 and held for about 1 to 3 hours at a temperature of about 50° C. to 85° C.

Further with respect to the third liquid/solid separation step 402, the liquefied solution (about 80-90% by volume), which includes oil, protein, and fine solids, is separated from the heavy solids cake (about 10-20% by volume), which includes the heavier fiber, grit, and germ. The dewatered solids portion of the stream at the third liquid/solid separation step 402 continues along the front end milling method and is next subjected to the third dewatered milling step 702 whereat the solids, particularly the germ and grit, are further reduced in size via size reduction equipment, then subjected to the second holding tank 115. At the second holding tank 115, the slurry is mixed with filtrate (less than 1 Brix of liquefied starch solution) from a fiber washing and dewatering step 706 and held for about 1 to 3 hours at a temperature of about 50° C. to 85° C.

The size reduction equipment utilized at the third dewatered milling step 702 can include a hammer mill, a pin or impact mill, a grind mill, and the like. In one example, the size reduction equipment is a pin mill or grind mill. This third dewatered milling step 702 is intended to further break the germ and grit particles and the bonds between fiber and starch, as well as oil and protein, without cutting the fiber too fine, thereby giving sharper separation between the fiber and protein/starch/oil. In a dewatered form, the germ and grit particles are able to break apart more easily than the fiber as a result of increased rubbing action in which less fine fiber is created, but the germ and grit are more fully milled. This results in a relatively non-uniform particle size amongst the milled solids. For example, germ and grit particles can be milled here to particle sizes between about 75 to 150 microns, whereas a majority of the fiber remains within a particle size range of 300 to 800 micron. In one example, greater than 75% of the fiber remains within a particle size range of 300 to 1000 micron. In another example, about 30% to about 75% by weight of the total particles after the third dewatered milling step 702 have a particle size from about 100 microns to about 800 microns. In still another example, about 40% to about 60% by weight of the total particles after the third dewatered milling step 702 have a particle size from about 100 microns to about 800 microns. In another example, no greater than 75% by weight of the total particles after the third dewatered milling step 702 have a particle size from about 100 microns to about 800 microns. In yet another example, no greater than 60% by weight of the total particles after the third dewatered milling step 702 have a particle size from about 100 microns to about 800 microns. In yet another example, no greater than 50% by weight of the total particles after the third dewatered milling step 702 have a particle size from about 100 microns to about 800 microns.

Various enzymes (and types thereof) such as amylase or glucoamylase, fungal, cellulose, cellobiose, protease, and the like can be optionally added after the third dewatered milling step 702 to enhance the separation of components, such as to help break the bonds between protein, starch, and fiber within the second holding tank 115, for example.

With continuing reference to FIG. 9, after the second holding tank 115, the slurry is sent and subjected to a fiber separation step 704, which helps to produce desirable fiber for secondary alcohol feed stock. Dewatering equipment, e.g., a paddle screen, vibration screen, filtration centrifuge, pressure screen, screen bowl decanter and the like, is used at the fiber separation step 704 to accomplish separation of the fiber from the liquefied starch solution. Again, the separated liquefied starch solution is recycled back and joins with the milled solids from the second dewatered milling step 502 whereat the germ and grit particles can be milled to particle sizes between about 45 to 300 microns. The separated fiber portion is forwarded on, mixed with cook water, then sent to fiber washing and dewatering step 706 whereat the fiber is washed and separated from the liquefied starch solution. The fiber washing and dewatering step 706 can utilize dewatering equipment, e.g., a paddle screen, vibration screen, fiber centrifuge, scroll screen, or conic screen centrifuge, pressure screen, preconcentrator, and the like, to accomplish separation of the solids from the liquid portion. In one example, the dewatering equipment is a paddle screen or a fiber centrifuge.

The washed/dewatered fiber from fiber washing and dewatering step 706 can be used as feed stock for secondary alcohol production. The resulting cellulosic material, which includes pericarp and tip cap and has more than 35% DS, less than 10% protein, less than 2% oil, and less than 1% starch/sugar, can be sent to a secondary alcohol system, as is known in the art, as feed stock without any further treatment. The cellulose yield is about 3 lb/bu.

The underflow from oil separation step 108, and optionally the oil polish step 109 and solvent extraction step 110, can be joined together and forwarded to the fermentation step 111. Although not depicted in FIG. 9, if the oil separation step 108 is not optionally utilized here, the underflow from the liquid/solid separation step 106 can be forwarded directly to the fermentation step 111. Because of the fiber washing and dewatering step 706 situated at the front end of the process, the size of the fermenter at fermentation step 111 may be decreased because it no longer needs to accommodate the bulk of the fiber component in the stream. Thereafter, at the distillation step 118, the sugar solution is separated from the "whole stillage", which includes protein, oil, and germ and grit particles and excludes fiber to a significant extent (less than 20% fiber), to produce alcohol. The whole stillage from the distiller tower includes only fine fiber because the coarse fiber has been removed at the fiber washing and dewatering step 706. The starch alcohol yield is about 2.82 gal/Bu, which is an increase of about 2.25% over conventional yields, due at least in part to the dewatered milling steps 112, 502, 702 whereat starch in the grit and germ is released and eventually converted to sugar to produce more alcohol.

As further shown in FIG. 9, the back end of the process 700 can include a fine fiber/protein separation step 708, which receives the stream from the distillation step 118. This stream is subjected to a special classification decanter or fine screen pressure screen, for example, to accomplish separation of the fine fiber from the liquid "thin stillage" portion, which includes protein. The separated fine fiber optionally can be sent to a caustic treatment step 710 whereat the fine fiber is treated with caustic, which includes a weak alkali solution (such as calcium, potassium, or sodium hydroxide, sodium carbonate, and the like), to adjust the pH to about 8.5 to 9.5 and separate residual bound proteins from the fine fiber. The treated fine fiber stream is forwarded to a fine fiber washing and dewatering step 712 whereat dewatering equipment, e.g., a paddle screen, vibration screen, filtration centrifuge, pressure screen, screen bowl decanter and the like, is used to accomplish separation of the fine fiber from the protein portion. The washed/dewatered fine fiber can be used as feed stock for secondary alcohol production, without any further treatment. The fine fiber yield is about 1 lb/bu, with less than 10% protein and less than 2% oil.

The filtrate from the fine fiber/protein separation step 708, which includes the protein, may be joined up with the residual protein separated at the fine fiber washing and dewatering step 712, then subjected to similar protein recovery and drying steps like those shown in FIG. 8. Further to that end, it is noted here that the fine protein recovery step 130 in the process 700 of FIG. 9 is optional. In addition, the heavier components from the optional fine protein recovery step 130 optionally can be subjected to centrifugation before being sent to a separate drying step (not shown), which utilizes a dryer, e.g., a ring dryer or the like, to yield a gluten/yeast mix (protein meal) having about 55% protein. Also, at drying step 124, a gluten/germ/fine fiber mix (protein meal) can be yielded having about 40% protein, which can be combined with the optional gluten/yeast mix (protein meal) having about 55% protein to produce a mixed protein meal having about 50% protein content and a yield of about 5.5 to 6 lb./Bu protein meal.

The liquid overflow from the optional fine protein recovery step 130 or the overflow from the protein recovery step 122 can move to evaporators at evaporation step 136 to separate any oil there from by boiling away moisture, leaving a thick syrup. Also, if the separated fine fiber is not subjected to the optional caustic treatment step 710 to yield cellulose for secondary alcohol, the centrifuged wet cake from washing and dewatering step 126 may be mixed with the syrup after evaporation step 136 and sold as DWGS, or further dried at drying step 140 and sold as DDGS.

The high concentrated syrup (more than 60% DS) from the evaporation step 136 can be used, amongst other things, as (a) nutrition for secondary alcohol production, (b) animal feed stock, (c) plant food, (d) and/or anaerobic digestion to produce biogas. The concentrated slurry optionally can be sent to a centrifuge, for example, to separate oil from the syrup at an oil recovery step. The oil can be sold as a separate high value product. In this process, a maximum oil yield of up to 1.2 lb/bu can be produced (about 0.8 lb/bu oil yield from the front end, and about 0.4 lb/bu oil yield from the back end). In yet another example, the concentrated syrup optionally can be mixed with the resulting fine germ and protein (as well as spent yeast) recovered from the protein recovery step 122, then sent to drying step 124 to yield a gluten/germ/yeast mix (protein meal) now including the syrup.

Figure 9A:
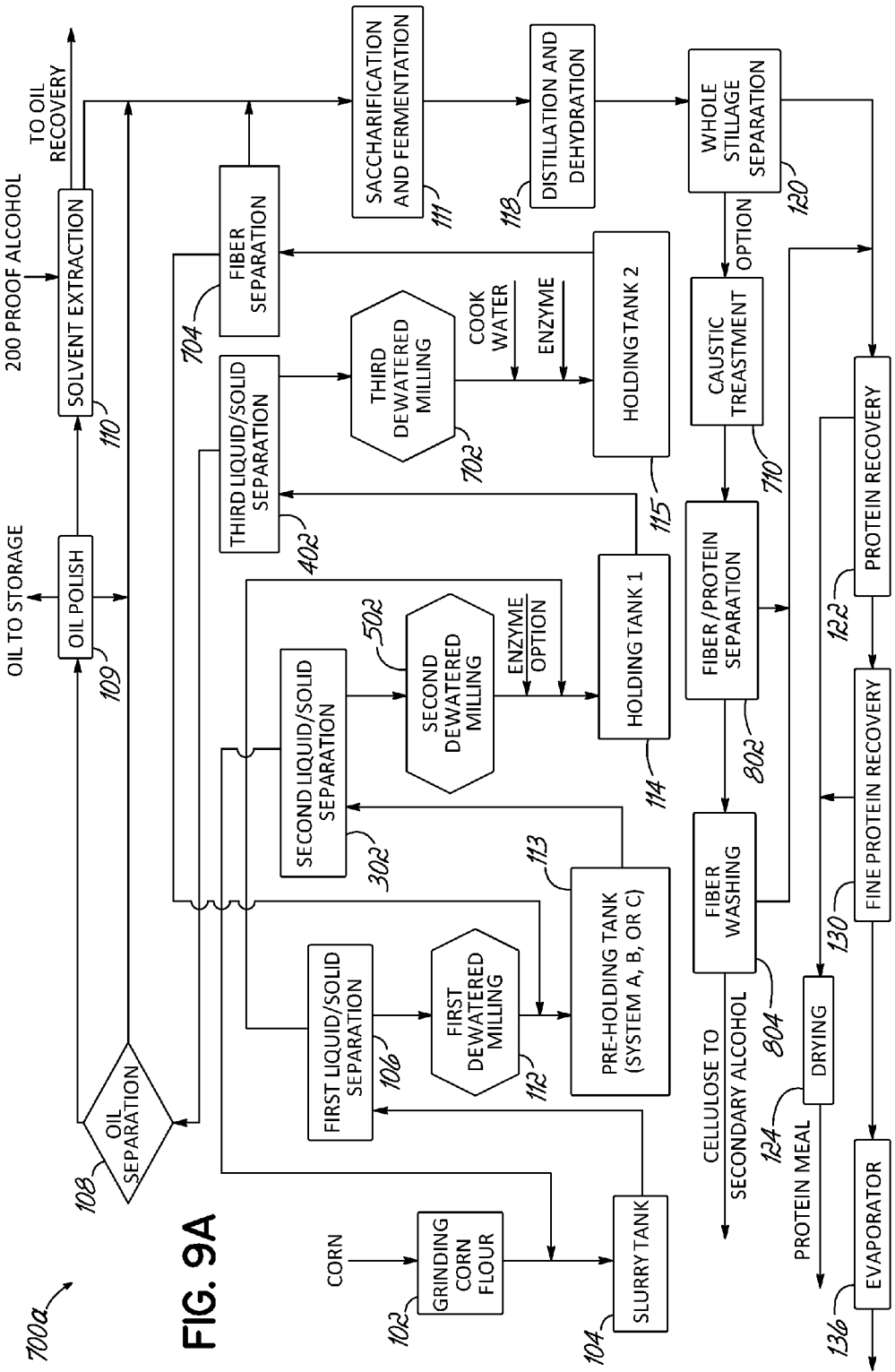
FIG. 9A is flow diagram showing a variation of the dry grind ethanol production process and system with front end milling method of FIG. 9 in accordance with another embodiment of the invention.

With reference now to FIG. 9A, this figure depicts a flow diagram showing a variation of the dry grind ethanol production process and system 700 with front end milling method of FIG. 9 in accordance with another embodiment of the invention for improving alcohol and/or byproduct yields, e.g., oil and/or protein yields. In this process 700A, at the front end, as compared to the process 700 of FIG. 9, the liquefied solution from the third liquid/solid separation step 402 optionally is sent to the oil separation step 108, rather than forwarded to join the milled solids after the first dewatered milling step 112. In turn, the filtrate from the fiber separation step 704 is recycled back in a counter current set up to join with the milled solids from the first dewatered milling step 112. Also, the liquefied solution (20 to 25 Brix) from the first liquid/solid separation step 106 is joined with the milled solids from the second dewatered milling step 502 and sent to the first holding tank 114, rather than forwarded to the optional oil separation step 108. Although not depicted in FIG. 9A, if the oil separation step 108 is not optionally utilized here, the liquefied solution from the third liquid/solid separation step 402 can be joined together with the fiber portion (fiber cake) from the fiber separation step 704 then subjected to the fermentation step 111.

With continuing reference to FIG. 9A, the fiber portion (fiber cake) from the fiber separation step 704 joins up with the heavy phase from the optional oil recovery step 108, and optionally the oil polish step 109 and the stream from the optional solvent extraction step 110, then subjected to the fermentation step 111. As such, the fiber washing and dewatering step 706 of FIG. 9 is eliminated. And the cook water that was added to the fiber portion from the fiber separation step 704 in FIG. 9 is now added to the milled solids from the third dewatered milling step 702 in the process 700A of FIG. 9A. The rest of the front end of the process 700A is generally the same as that of FIG. 9.

With further reference to FIG. 9A, the back end of the process 700A can include, after the distillation step 118, the whole stillage separation step 120 whereat dewatering equipment, e.g., a paddle screen, vibration screen, filtration centrifuge, pressure screen, screen bowl decanter and the like, is used to accomplish separation of the insoluble solids or "whole stillage", which includes fiber, from the liquid "thin stillage" portion. The separated fiber optionally can be sent to caustic treatment step 710 whereat the fiber is treated with caustic, which includes a weak alkali solution (such as calcium, potassium, or sodium hydroxide, or sodium carbonate, and the like), to adjust the pH to about 8.5 to 9.5 and separate residual bound proteins from the fiber. A high shear jet cooker or dewatered milling device may optionally be utilized in the caustic treatment step 710.

The treated fiber stream is forwarded to a fiber/protein separation step 802 whereat dewatering equipment, e.g., a paddle screen, vibration screen, filtration centrifuge, pressure screen, screen bowl decanter and the like, is used to accomplish separation of the fiber from the protein portion. The separated fiber is next subjected to a fiber washing step 804, and the washed fiber can be used as feed stock for secondary alcohol production, without any further treatment. This secondary alcohol production from cellulose is understood to meet government requirements for year 2014 for alcohol produced from starch, which must mix 10% of alcohol produced from cellulose.

The filtrate from the fiber/protein separation step 802 and the fiber washing step 804 is mixed together and the pH adjusted to 5 to 6 by treating the filtrate with sulfuric acid, hydrochloric acid, phosphoric acid, or the like. The filtrate is then joined with the liquid "thin stillage" portion from the whole stillage separation step 120, and subjected to protein recovery step 122, followed by the fine protein recovery step 130, like that of FIG. 9. 50% protein is realized at dryer step 124. The centrate from the fine protein recovery step 130 is sent to evaporator 136 whereat water is removed to produce 60% DS syrup. The DDGS dryer step 140 is eliminated in the process 700A of FIG. 9A.

Figure 9B:
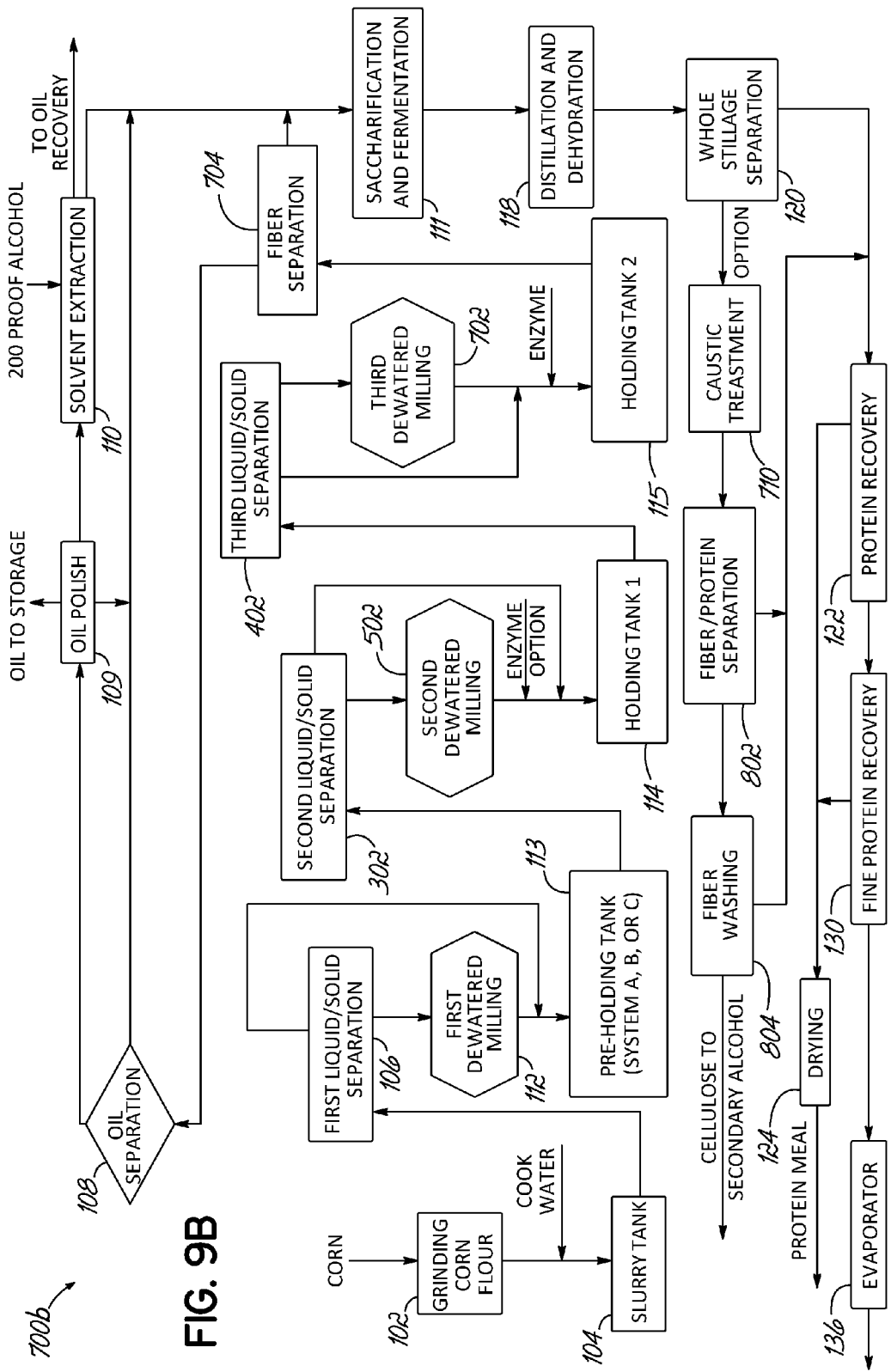
FIG. 9B is flow diagram showing a variation of the dry grind ethanol production process and system with front milling method of FIG. 9A in accordance with another embodiment of this invention.

With reference now to FIG. 9B, this figure depicts a flow diagram showing a variation of the dry grind ethanol production process and system 700A with front end milling method of FIG. 9A in accordance with another embodiment of the invention for improving alcohol and/or byproduct yields, e.g., oil and/or protein yields. In this process 700B, the counter current washing of FIG. 9A, which includes removing and recycling back within the process 700A the liquefied starch plus certain sized solids from the slurry stream at the second liquid/solid separation step 302, the third liquid/solid separation step 402, and the fiber separation step 704, is eliminated. Instead, the ground corn flour in the process 700B is again mixed with initial cook water at the slurry tank 104 to create a slurry and begin liquefaction, as in FIG. 3. In turn, the filtrate from the third liquid/solid separation step 402 is joined up with the milled solids from the third dewatered milling step 702 rather than forwarded to oil separation step 108.

In addition, the filtrate from the fiber separation step 704 is now sent to the oil separation step 108 rather than recycled back to join with the milled solids from the first dewatered milling step 112. Also, the filtrate from the second liquid/solid separation step 302 is joined up with the milled solids from the second dewatered milling step 502 rather than mixed with the ground corn flour just prior to slurry tank 104. And the liquefied solution from the first liquid/solid separation step 106 is similarly joined up with the milled solids from the first dewatered milling step 112. Although not depicted in FIG. 9A, if the oil separation step 108 is not optionally utilized here, the fiber separation step 704 may be eliminated and the liquefied starch slurry solution is sent directly from the second holding tank 115 to fermentation step 111. The rest of the dry grind ethanol production process 700B is generally the same as that of FIG. 9A.

The processes of the present invention, as shown in FIGS. 3-9B can include, for example, up to three dewatered milling steps depending on the desired alcohol, oil, protein, and fiber yield and purity level. And with the current dry mill process, the germ and grit particles still exist after distillation and then combine together as low value byproduct DDGS, which includes about 30% protein, 10% oil, and 5% starch. However, the dry grind ethanol production processes, with front end grinding method, break up the bonds between fiber, protein, oil, and starch in the grit, germ and fiber (pericarp and tip cap) to produce valuable byproducts such as oil, protein, extra alcohol from starch and cellulose. Indeed, instead of low value DDGS, the processes of FIGS. 3-9B can be used to produce desirable byproducts, including oil, protein, and cellulose.

While the present invention has been illustrated by a description of various embodiments and while these embodiments have been described in considerable detail, it is not the intention of the applicant to restrict or in any way limit the scope of the appended claims to such detail. For example, although the various systems and methods described herein have focused on corn, virtually any type of grain, including, but not limited to, wheat, barley, sorghum, rye, rice, oats and the like, can be used. Also, for example, for the optional oil separation step 108, the feed may be taken from the slurry tank 104, pre-holding tank step 113, or from the first or second holding tank step 114, 115. And more broadly speaking, it should be understood that the flow diagrams can be modified, for example, to include or exclude counter current washing and front end oil recovery, to vary the location of the dewatered milling step(s), to produce fiber for secondary alcohol production (front end or back end), and to separate protein from fiber and produce high protein meal. In addition, alcohol production and recovery can be considered to be optional steps and may be excluded from the process. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A dry grind ethanol production process, the process comprising:
(A) grinding dry corn kernels into corn flour;
(B) mixing the ground corn flour with a liquid to produce a slurry including free oil, protein, starch, and fiber, germ, and grit particles;
(C) subjecting the slurry of step (B) to the start of liquefaction, which includes adding an enzyme to the slurry;
(D) after step (C), separating the slurry, via particle sizes alone, into a solids portion, separately including the fiber, grit, and germ particles of the slurry, and a liquid portion, including the free oil, protein, and starch of the slurry;
(E) milling the separated solids portion of step (D) to reduce the size of the fiber, grit, and germ particles and release starch, oil, and protein therefrom;

(F) recombining at least the starch from the separated liquid portion of step (D) with at least the released starch of step (E) to form a second slurry;

(G) converting the starches in the second slurry of step (F) to sugar;

(H) producing alcohol from the sugar of step (G) via fermentation; and (I) recovering the alcohol after fermentation.

2. The process of claim 1 further comprising separating and recovering the fiber from any of steps (A) through (I).

3. The process of claim 2, wherein the fiber of any of steps (A) through (G) is separated and recovered prior to step (H).

4. The process of claim 2 wherein separating remaining fiber after step (H) further comprises subjecting said remaining fiber to a caustic treatment and recovering the treated fiber.

5. The process of claim 1 further comprising, prior to producing alcohol from the sugar and recovering the alcohol, separating and recovering the free oil from the liquid portion of step (D).

6. The process of claim 5 wherein separating and recovering the free oil from the liquid portion of step (D) includes extracting the oil from the liquid portion of step (D) via solvent extraction.

7. The process of claim 1 wherein said process comprises counter-current washing.

8. The process of claim 1 wherein step (E) further comprises the following:

(E1) separating the milled solids portion of step (E) into a second solids portion, including the fiber, grit, and germ particles of the milled solids portion of step (E), and a second liquid portion, including the released oil, protein, and starch of the milled solids portion of step (E).

9. The process of claim 8 wherein step (E1) further comprises the following:

(E2) after separating the milled solids portion of step (E) into the second solids portion and the second liquid portion, further separating the second solids portion into an additional solids portion, including the fiber, grit, and germ particles of the second solids portion, and an additional liquid portion, including the released oil, protein, and starch of the second solids portion.

10. The process of claim 9 further comprising separating and recovering the released oil from the additional liquid portion prior to producing alcohol from the sugar and recovering the alcohol.

11. The process of claim 8 wherein step (E1) further comprises the following:

(E3) milling the second solids portion of step (E1) to reduce the size of the fiber, grit, and germ particles and release starch, oil, and protein therefrom.

12. The process of claim 11 wherein step (E3) further comprises the following:

(E4) separating the milled second solids portion of step (E3) into a third solids portion, including the fiber, grit, and germ particles of the milled second solids portion of step (E3), and a third liquid portion, including the released oil, protein, and starch of the milled second solids portion of step (E3).

13. The process of claim 12 wherein step (E4) further comprises the following:

(E5) milling the third solids portion of step (E4) to reduce the size of the fiber, grit, and germ particles and release starch, oil, and protein therefrom.

14. The process of claim 1 further comprising separating and recovering the protein from the liquid portion of step (D) and/or the protein from the milled solids portion of step (E).

15. The process of claim 14 wherein the protein from the liquid portion of step (D) and/or the protein from the milled solids portion of step (E) is separated and recovered after step (I).

16. A dry grind ethanol production process, the process comprising:

(A) grinding dry corn kernels into corn flour;

(B) mixing the ground corn flour with a liquid to produce a slurry including free oil, protein, starch, and fiber, germ, and grit particles;

(C) subjecting the slurry of step (B) to the start of liquefaction, which includes adding an enzyme to the slurry;

(D) after step (C), separating the slurry, via particle sizes alone, into a solids portion, separately including the fiber, grit, and germ particles of the slurry, and a liquid portion, including the free oil, protein, and starch of the slurry;

(E) milling the separated solids portion of step (D) to reduce the size of the fiber, grit, and germ particles and release starch, oil, and protein therefrom;

(F) separating the milled solids portion of step (E) into a second solids portion, including the fiber, grit, and germ particles of the milled solids portion of step (E), and a second liquid portion, including the released oil, protein, and starch of the milled solids portion of step (E);

(G) recombining at least the starch from the separated liquid portion of step (D) with at least the released starch of step (E) to form a second slurry;

(H) converting the starches in the second slurry of step (G) to sugar;

(I) producing alcohol from the sugar of step (H) via fermentation;

(J) recovering the alcohol after fermentation;

(K) grinding a second portion of dry corn kernels into a second corn flour;

(L) mixing the second corn flour with the second liquid portion of step (F) to produce a third slurry including free oil, protein, starch, and fiber, germ, and grit particles;

(M) subjecting the third slurry of step (L) to the start of liquefaction, which includes adding an enzyme to the third slurry;

(N) after step (M), separating the third slurry, via particle sizes alone, into a third solids portion, separately including the fiber, grit, and germ particles of the third slurry, and a third liquid portion, including the free oil, protein, and starch of the third slurry;

(O) milling the separated third solids portion of step (N) to reduce the size of the fiber, grit, and germ particles and release starch, oil, and protein therefrom;

(P) recombining at least the starch from the separated third liquid portion of step (N) with at least the released starch of step (O) to form a fourth slurry;

(Q) converting the starches in the fourth slurry of step (P) to sugar;

(R) producing alcohol from the sugar of step (Q) via fermentation;

(S) recovering the alcohol after fermentation.

17. The process of claim 1, wherein the alcohol is ethanol.

18. The process of claim 16, wherein the alcohol is ethanol.

* * * * *

UNITED STATES PATENT AND TRADEMARK OFFICE
CERTIFICATE OF CORRECTION

PATENT NO.         : 9,012,191 B2
APPLICATION NO.    : 13/428263
DATED              : April 21, 2015
INVENTOR(S)        : Chie Ying Lee Page 1 of 1

It is certified that error appears in the above-identified patent and that said Letters Patent is hereby corrected as shown below:

In the Claims:

Claim 1, Column 24, line 53, replace "A dry grind ethanol production process," with -- A dry grind alcohol production process, --

Claim 16, Column 26, line 8, replace "A dry grind ethanol production process," with -- A dry grind alcohol production process. --

Signed and Sealed this
Sixth Day of October, 2015

Michelle K. Lee
*Director of the United States Patent and Trademark Office*